(12) United States Patent
Knudson et al.

(10) Patent No.: US 7,717,875 B2
(45) Date of Patent: May 18, 2010

(54) STEERABLE CATHETER WITH HYDRAULIC OR PNEUMATIC ACTUATOR

(75) Inventors: John Christian Knudson, Chanhassen, MN (US); Andrew Thomas Forsberg, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 645 days.

(21) Appl. No.: 10/895,510

(22) Filed: Jul. 20, 2004

(65) Prior Publication Data

US 2006/0084964 A1  Apr. 20, 2006

(51) Int. Cl.
 *A61M 37/00* (2006.01)
(52) U.S. Cl. .............. 604/95.04; 604/95.01; 604/95.03
(58) Field of Classification Search .............. 604/94.01, 604/95.01–95.05, 523–532, 96.01, 164.01
See application file for complete search history.

(56) References Cited

U.S. PATENT DOCUMENTS

| | | | |
|---|---|---|---|
| 3,605,745 A * | 9/1971 | Hodosh | 604/143 |
| 4,826,087 A * | 5/1989 | Chinery | 239/551 |
| 4,838,859 A * | 6/1989 | Strassmann | 604/95.03 |
| 5,125,896 A | 6/1992 | Hojeibane | |
| 5,242,441 A | 9/1993 | Avitall | |
| 5,263,493 A | 11/1993 | Avitall | |
| 5,269,757 A | 12/1993 | Fagan et al. | |
| RE34,502 E | 1/1994 | Webster, Jr. | |
| 5,277,199 A | 1/1994 | DuBois et al. | |
| 5,281,217 A | 1/1994 | Edwards et al. | |
| 5,318,525 A | 6/1994 | West et al. | |
| 5,327,905 A | 7/1994 | Avitall | |
| 5,330,466 A | 7/1994 | Imran | |
| 5,354,297 A | 10/1994 | Avitall | |
| 5,383,923 A | 1/1995 | Webster, Jr. | |
| 5,389,073 A | 2/1995 | Imran | |
| 5,391,147 A | 2/1995 | Imran et al. | |
| 5,395,329 A | 3/1995 | Ockuly et al. | |
| 5,397,304 A | 3/1995 | Truckai | |
| 5,431,168 A | 7/1995 | Webster, Jr. | |
| 5,478,330 A | 12/1995 | Imran et al. | |
| 5,487,757 A | 1/1996 | Truckai | |
| 5,527,279 A | 6/1996 | Imran | |
| 5,533,967 A | 7/1996 | Imran | |
| 5,545,200 A | 8/1996 | West | |
| 5,562,619 A | 10/1996 | Mirarchi et al. | |
| 5,582,609 A | 12/1996 | Swanson et al. | |
| 5,588,964 A | 12/1996 | Imran et al. | |
| 5,611,777 A | 3/1997 | Bowden et al. | |

(Continued)

OTHER PUBLICATIONS

International Search Report for PCT/US05/25888, filed Jul. 20, 2005, with Written Opinion dated Feb. 29, 2008.

*Primary Examiner*—Kevin C Sirmons
*Assistant Examiner*—Phillip Gray
(74) *Attorney, Agent, or Firm*—Wiley Rein LLP

(57) ABSTRACT

A hydraulically assisted actuator in a handle connects with a catheter having a deflectable distal ablation tip. The hydraulic actuator translates small mechanical movement by a clinician into large travel movements of connected steering cables and increased tension in the ablation tip for greater deflection. The hydraulic system further dampens the return of the ablation tip from a deflected position to an equilibrium position. The hydraulic actuation system is also incorporated into a set of foot pedals.

20 Claims, 13 Drawing Sheets

U.S. PATENT DOCUMENTS

| | | | |
|---|---|---|---|
| 5,656,029 A | 8/1997 | Imran et al. |
| 5,656,030 A | 8/1997 | Hunjan et al. |
| 5,715,817 A | 2/1998 | Stevens-Wright et al. |
| 5,755,760 A | 5/1998 | Maguire |
| 5,779,669 A | 7/1998 | Haissaguerre et al. |
| 5,807,249 A | 9/1998 | Qin et al. |
| 5,823,955 A | 10/1998 | Kuck et al. |
| 5,826,576 A | 10/1998 | West |
| 5,836,947 A | 11/1998 | Fleischman et al. |
| 5,861,024 A | 1/1999 | Rashidi |
| 5,865,800 A | 2/1999 | Mirarchi et al. |
| 5,868,741 A | 2/1999 | Chia et al. |
| 5,876,399 A | 3/1999 | Chia et al. |
| 5,885,278 A | 3/1999 | Fleischman |
| 5,897,529 A | 4/1999 | Ponzi |
| 5,897,554 A | 4/1999 | Chia et al. |
| 5,910,129 A | 6/1999 | Koblish |
| 5,913,854 A | 6/1999 | Maguire et al. |
| 5,916,213 A | 6/1999 | Haissaguerre et al. |
| 5,916,214 A | 6/1999 | Cosio et al. |
| 5,919,188 A | 7/1999 | Shearon et al. |
| 5,931,811 A | 8/1999 | Haissaguerre et al. |
| 5,935,102 A | 8/1999 | Bowden et al. |
| 5,938,603 A | 8/1999 | Ponzi |
| 5,944,690 A | 8/1999 | Falwell et al. |
| 5,951,471 A | 9/1999 | Rama et al. |
| 5,964,796 A | 10/1999 | Imran |
| 5,987,344 A | 11/1999 | West |
| 6,014,579 A | 1/2000 | Pomeranz et al. |
| 6,023,638 A | 2/2000 | Swanson |
| 6,027,473 A | 2/2000 | Ponzi |
| 6,048,329 A | 4/2000 | Thompson et al. |
| 6,059,739 A | 5/2000 | Baumann |
| 6,063,022 A | 5/2000 | Ben-Haim |
| 6,064,902 A | 5/2000 | Haissaguerre et al. |
| 6,066,125 A | 5/2000 | Webster, Jr. |
| 6,071,282 A | 6/2000 | Fleischman |
| 6,083,222 A | 7/2000 | Klein et al. |
| 6,123,699 A | 9/2000 | Webster, Jr. |
| 6,146,338 A | 11/2000 | Gardeski et al. |
| 6,149,663 A | 11/2000 | Strandberg et al. |
| 6,171,277 B1 | 1/2001 | Ponzi |
| 6,178,354 B1 | 1/2001 | Gibson |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,200,315 B1 | 3/2001 | Gaiser et al. |
| 6,203,507 B1 | 3/2001 | Wadsworth et al. |
| 6,203,525 B1 | 3/2001 | Whayne et al. |
| 6,210,362 B1 | 4/2001 | Ponzi |
| 6,210,407 B1 | 4/2001 | Webster, Jr. |
| 6,212,426 B1 | 4/2001 | Swanson |
| 6,214,002 B1 | 4/2001 | Fleischman et al. |
| 6,221,087 B1 | 4/2001 | Anderson |
| 6,224,587 B1 | 5/2001 | Gibson |
| 6,241,754 B1 | 6/2001 | Swanson et al. |
| 6,314,962 B1 | 11/2001 | Vaska et al. |
| 6,330,473 B1 | 12/2001 | Swanson et al. |
| 6,402,746 B1 | 6/2002 | Whayne et al. |
| 6,454,758 B1 | 9/2002 | Thompson et al. |

\* cited by examiner

STEERABLE CATHETER WITH HYDRAULIC OR PNEUMATIC ACTUATOR

BACKGROUND OF THE INVENTION a. Field of the Invention

This invention is directed to an actuator for steering the distal end of a catheter. In particular, the actuator incorporates a hydraulic control system to provide for a larger range of travel of steering cables and for finer control of the distal end of the catheter.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

Catheters are also used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart.

A typical human heart includes a right ventricle, a right atrium, a left ventricle, and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In the normal heart, contraction and relaxation of the heart muscle (myocardium) takes place in an organized fashion as electro-chemical signals pass sequentially through the myocardium from the sinoatrial (SA) node, which comprises a bundle of unique cells disposed in the wall of the right atrium, to the atrioventricular (AV) node and then along a well-defined route, which includes the His-Purkinje system, into the left and right ventricles. The AV node lies near the ostium of the coronary sinus in the interatrial septum in the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole, wherein the atria contract to empty and fill blood into the ventricles. The atrial depolarization from the SA node is detected by the AV node which, in turn, communicates the depolarization impulse into the ventricles via the bundle of His and Purkinje fibers following a brief conduction delay. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia is catheter ablation. During conventional catheter ablation procedures, an energy source is placed in contact with cardiac tissue to heat the tissue and create a permanent scar or lesion that is electrically inactive or noncontractile. During one procedure, the lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). Ablation of fast or slow AV nodal pathways is disclosed in Singer, I., et al., "Catheter Ablation for Arrhythmias," Clinical Manual of Electrophysiology, pgs. 421-431 (1993).

Another medical procedure using ablation catheters with sheaths to ablate accessory pathways associated with W-P-W utilizing both a transseptal and retrograde approach is discussed in Saul, J. P., et al., "Catheter Ablation of Accessory Atrioventricular Pathways in Young Patients: Use of long vascular sheaths, the transseptal approach and a retrograde left posterior parallel approach," Journal of the American College of Cardiology, Vol. 21, no. 3, pgs. 571-583 (1 Mar. 1993). Other catheter ablation procedures are disclosed in Swartz, J. F., "Radiofrequency Endocardial Catheter Ablation of Accessory Atrioventricular Pathway Atrial Insertion Sites," Circulation, Vol. 87, no. 2, pgs. 487-499 (Feb 1993).

Ablation of a specific location within or near the heart requires the precise placement of the ablation catheter. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart, which are marked by radiopaque diagnostic catheters that are placed in or at known anatomical structures, such as the coronary sinus, high right atrium, and the right ventricle).

Typically, the main body of an ablation catheter is a flexible tube constructed from polyurethane, nylon, or some other electrically non-conductive, flexible material with braided steel wires or other non metallic fibers in its wall as reinforcing elements. In order to precisely place the distal tip of a catheter to conduct an ablation procedure, catheters may have a deflectable distal tip. The distal portion of deflectable tip catheters is typically made from non-braided flexible tube. This portion can be deformed into a variety of curved configurations with different radii of curvature by means of user input to a manual actuator on the catheter handle. The actuator is commonly internally linked to the distal tip by at least one tension or pull cable.

The proximal end of the tension or pull cable(s) is generally connected to a tensioning or puller mechanism in the handle. The distal end of the tension or pull cable(s) is fixed or anchored to a point in the distal tip. The tensioning mechanism generally includes a manual actuator by which the distal tip can be deflected. The primary difference among the designs of deflectable distal tip catheters is in the tension or pull mechanism in the catheter handle. This mechanism transmits the manual force applied to the actuator on the handle to the distal tip via the cable(s), for formation of a desirable radius of curvature at the distal tip of the catheter.

Unfortunately, many of the manual actuator designs require significant manual force to effect the necessary tension on the cable(s) to bend the distal tip. In addition, the presently available actuators are unable to provide enough travel distance when pulling the cable(s) to deflect the distal tip a desired amount. Further, the present manual actuators do not provide the ability to either hold the distal tip in a deflected position or to dampen the return of the distal tip from a deflected position to a "straight" position.

The information included in this Background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is directed to a hydraulically assisted actuator in a handle for operating a catheter with a deflectable distal ablation tip. The hydraulic actuator translates small mechanical movement by a clinician into large travel movements of the steering cables and increase tension in the ablation tip of the catheter for greater deflection. The hydraulic system further dampens the return of the ablation tip from a deflected to an equilibrium position. In an alternate embodiment, the hydraulic actuation system is incorporated into a set of foot pedals.

In one embodiment of the invention, an actuator assembly for a steerable catheter is composed of a hydraulic system and a mechanical actuator. The hydraulic system has a master cylinder, at least one slave cylinder fluidly coupled with the master cylinder, and at least one steering cable operably connected at a first end with the at least one slave cylinder and operably connected at a second end with a distal tip of a catheter. The mechanical actuator is operably connected with the master cylinder and imparts a mechanical force to the master cylinder. The mechanical force of the actuator is translated into fluid force within the master cylinder and, by coupling with the at least one slave cylinder, into fluid force within the at least one slave cylinder. The fluid force within the at least one slave cylinder is then translated into a tensile force on the at least one steering cable.

In a particular embodiment, the at least one slave cylinder is composed of a first slave cylinder and a second slave cylinder. The at least one steering cable is also composed of a first steering cable and a second steering cable. The first steering cable is operably connected at a proximal end with the first slave cylinder and operably connected at a distal end with the distal tip of the catheter. The second steering cable is operably connected at a proximal end with the second slave cylinder and operably connected at a distal end with the distal tip of the catheter.

Another aspect of the invention is a method for bending a distal tip of a catheter. A mechanical actuator connected with a master cylinder is operated. Fluid within the master cylinder is pressurized to push a master piston within the master cylinder in a first direction. A first portion of the fluid within the master cylinder is caused to enter into a first slave cylinder. A first slave piston in the first slave cylinder is pushed in a second direction. A first steering cable is connected at a proximal end with the first slave piston and connected at a distal end with the distal tip of the catheter. Tension on the first steering cable is thus increased. The distal tip of the catheter is bent in a first direction as a result of the step of increasing the tension on the first steering cable. Alternately, the fluid within the master cylinder is pressurized to push the master piston within the master cylinder in a second direction. A second portion of the fluid within the master cylinder is caused to enter into a second slave cylinder. A second slave piston in the second slave cylinder is pushed in the second direction. A second steering cable is connected at a proximal end with the second slave piston and connected at a distal end with the distal tip of the catheter. Tension on the second steering cable is thereby increased. The distal tip of the catheter is bent in a second direction as a result of the step of increasing the tension on the second steering cable.

In a further embodiment of the invention, an actuator assembly for a steerable catheter is composed of a pneumatic system and a mechanical actuator. The pneumatic system has a master cylinder and at least one slave cylinder fluidly coupled with both the master cylinder and a distal tip of a catheter. The mechanical actuator is operably connected with the master cylinder and imparts a mechanical force to the master cylinder, which increases fluid pressure in the at least one slave cylinder and deflects the distal tip of the catheter.

Other features, utilities and advantages of various embodiments of the invention will be apparent from the following more particular description of embodiments of the invention as illustrated in the accompanying drawings and defined in the appended claims.

DETAILED DESCRIPTION OF THE INVENTION

The present invention is a hydraulically assisted mechanical actuator for operating a catheter with a deflectable distal tip. A hydraulic system within a handle translates small mechanical movements of a mechanical actuator by a clinician into large travel movements of steering cables connected with the distal tip of the catheter. The greater travel of the steering cables increases the tension placed by the steering cables on the distal tip of the catheter over tension achieved by a purely mechanical actuator and results in greater deflection of the distal tip. The greater travel distance achieved by the hydraulic system also provides for finer control of the deflection of the distal tip of the catheter. The hydraulic system further dampens the return of the distal tip from a deflected to an equilibrium position.

Figure 1:
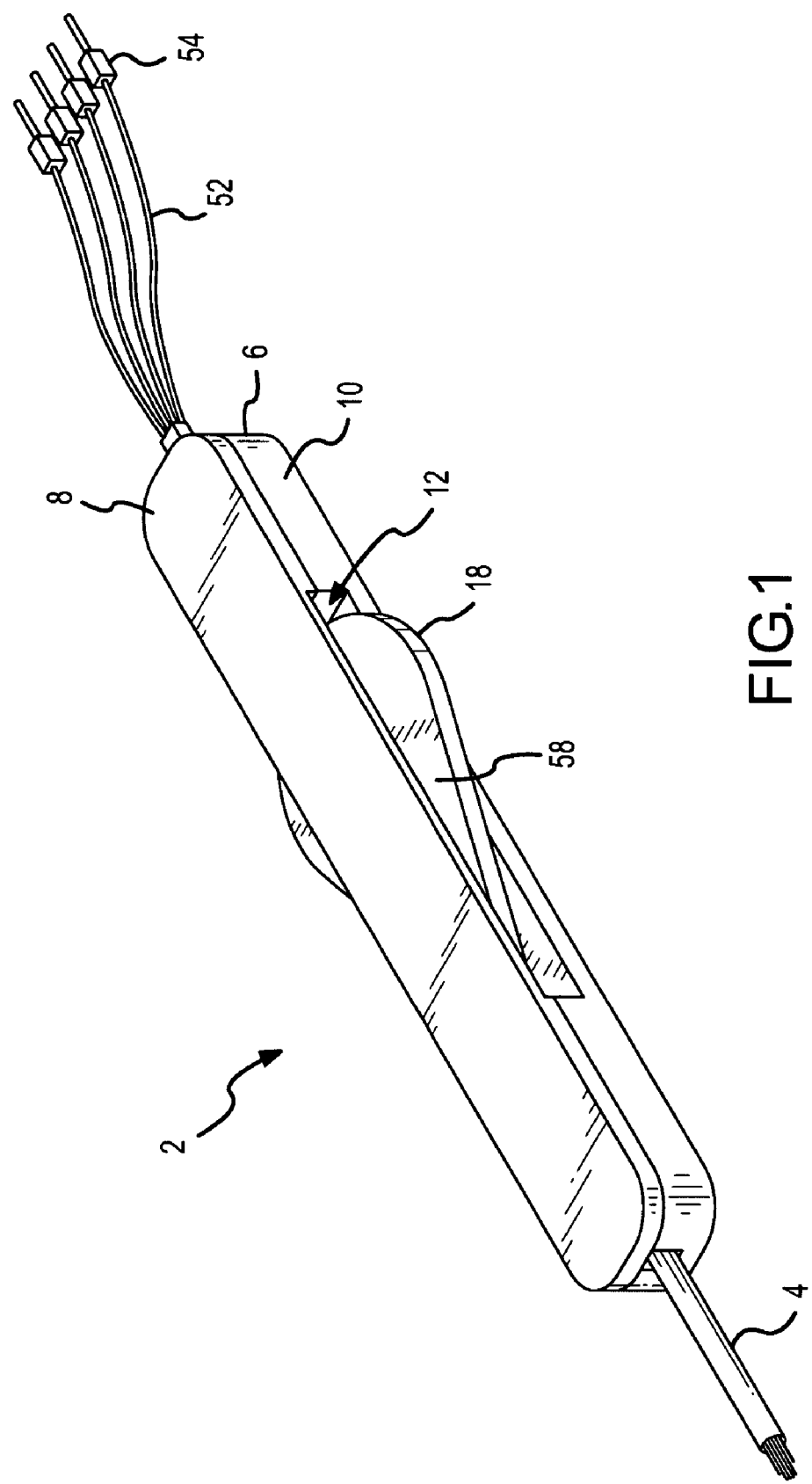
FIG. 1 is an isometric view of an actuator assembly for a steerable catheter according to a first embodiment of the present invention.

FIGS. 1-5 depict a first embodiment of a steerable catheter with a hydraulic actuator according to the present invention. In FIG. 1, the actuator assembly 2 is shown in detail and is primarily encased by an actuator handle 6, which itself is composed of a handle cap 8 and a handle base 10. The handle base 10 and the handle cap 8 are joined together by a common interface and between them define a handle bay 12 within which a pivot actuator 18 is housed. The handle cap 6 and the handle base 8 may be composed of a molded plastic material and may be joined together, for example, by ultrasonic welding, after the installation of the internal components.

Figure 2:
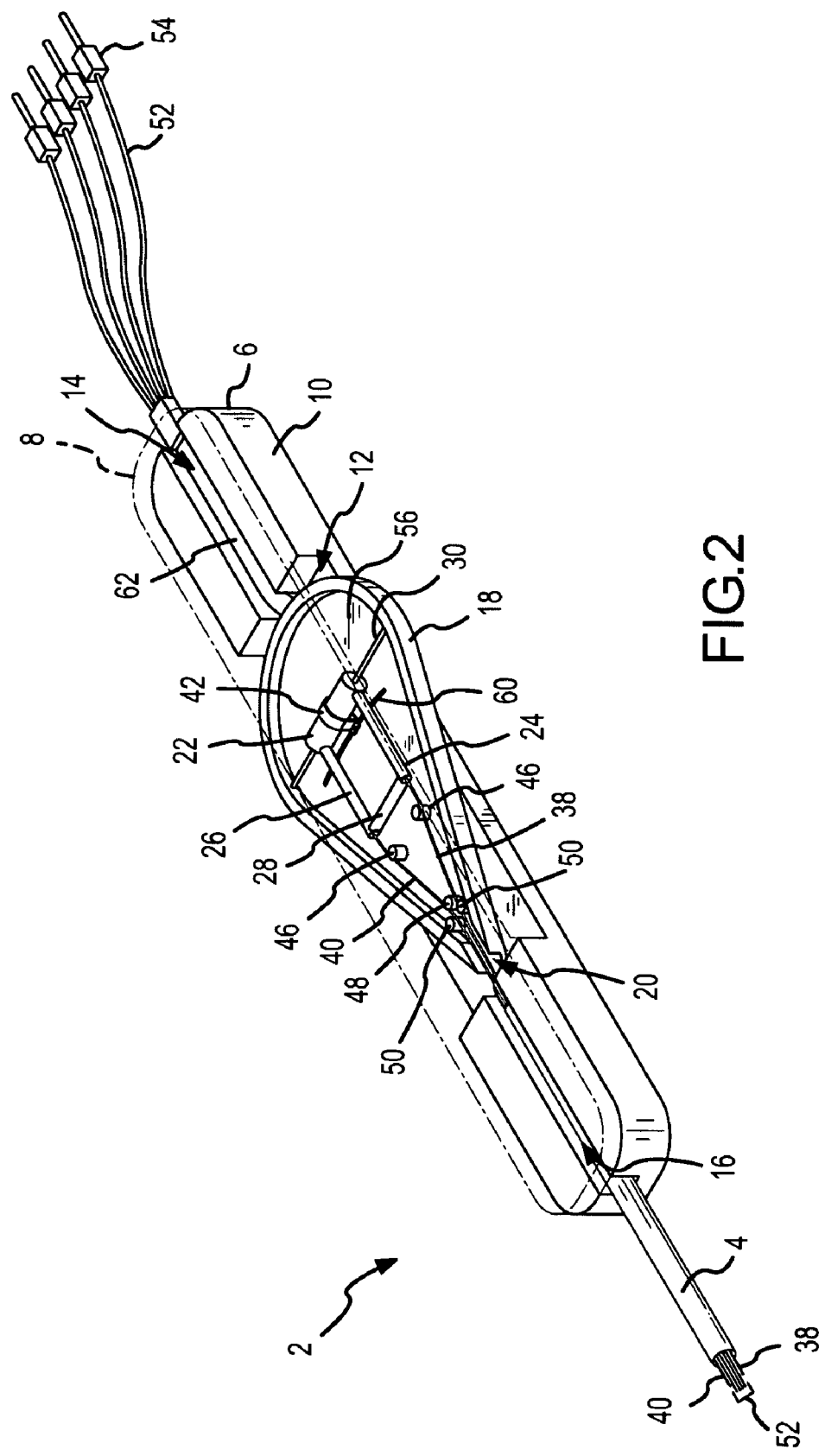
FIG. 2 is an isometric view of the actuator assembly of FIG. 1, wherein the handle cap and the top actuator panel are depicted in phantom to reveal the internal components of the actuator assembly.
Figure 3:
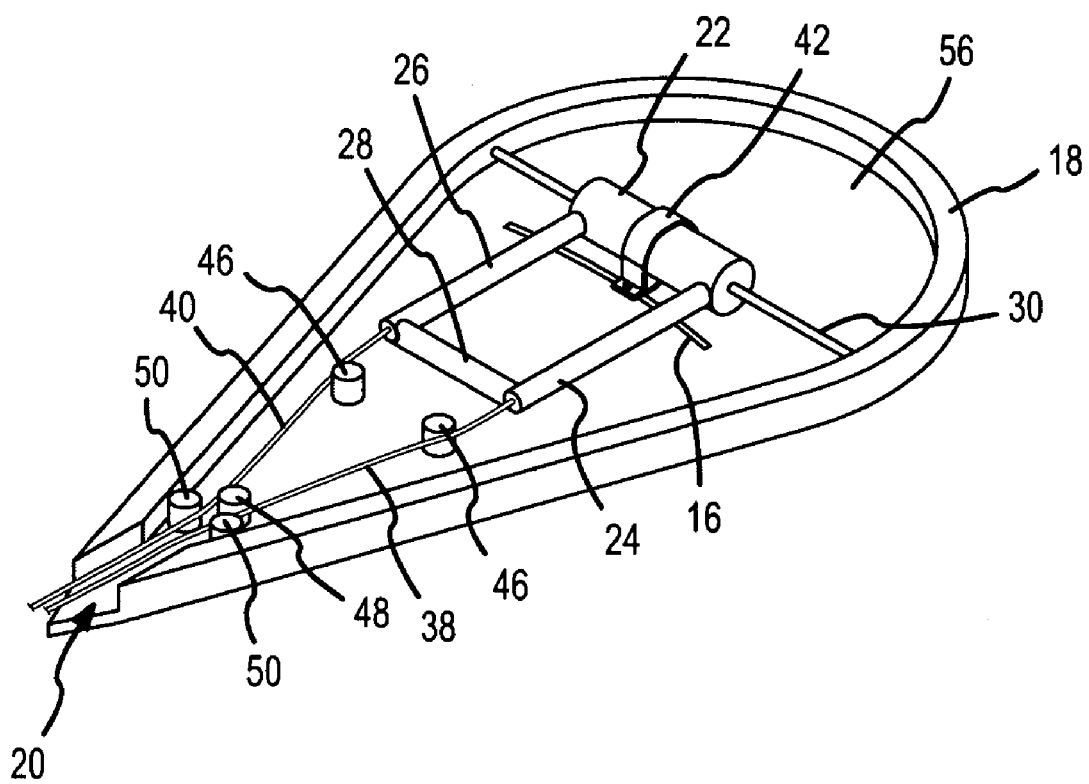
FIG. 3 is an isometric view of the pivot actuator and hydraulic components of the actuator assembly of FIG. 1.

The actuator assembly 2 according to the present invention is depicted to good advantage in FIG. 2 with the handle cap 8 of the actuator handle 6 shown transparently to provide a clear view of the interior components of the actuator assembly 2. As shown to good advantage in FIGS. 1, 3, and 4, the pivot actuator 18 is formed as a tear-drop shaped wall defining a chamber 19 within which is housed a variety of additional components. The pivot actuator 18 may be enclosed on a bottom side by a bottom actuator panel 56 and on the top side by a top actuator panel 58 (see FIG. 1). The bottom actuator panel 56 and the top actuator panel 58 are provided to protect the components within the pivot actuator 18 from environmental conditions, for example, dust and fluid, that may inhibit the operation of the actuator assembly 2. The pivot actuator 18, the bottom actuator panel 56, and the top actuator panel 58 may all be composed of molded plastic materials. The pivot actuator 18 and the bottom actuator panel 56 may be of a unitary molded construction or they may be separate components joined together, for example, via an ultrasonic weld. Once the components are installed within the chamber 19 formed by the pivot actuator 18 and the bottom actuator panel 56 and the pivot actuator 18 is installed within the handle bay 12, the top actuator panel 58 may be placed upon ultrasonically welded to the pivot actuator 18.

As shown in FIGS. 2-4C, a hydraulic system is installed within the chamber 19 formed by the pivot actuator 18. A master shaft 30 spans the widest part of the bulbous area of the tear-drop shaped pivot actuator 18. Each end of the master shaft 30 is mounted on opposing internally facing surfaces of the pivot actuator 18. The master shaft 30 travels through a master cylinder 22, which is a relatively large diameter hydraulic cylinder filled with hydraulic fluid. The master shaft 30 extends laterally through apertures in the lateral ends of the master cylinder 22. Sealing members, for example O-rings, may be positioned within the apertures in the lateral ends of the master cylinder 22 to seal against the master shaft 30 to prevent fluid from leaking out of the master cylinder 22 through the interface between the master shaft 30 and the apertures. A master piston 32 is affixed to the master shaft 30 within the master cylinder 22 equidistant from each end of the master shaft 30. The master piston 32 engages the interior walls of the master cylinder 22 to create a fluid-tight seal therewith and is adapted to travel axially within the master cylinder 22 when motivated by the pivot actuator 18 and the master shaft 30.

A first slave cylinder 24 and a second slave cylinder 26 are physically mounted orthogonally to the cylindrical side wall of the master cylinder 22 adjacent respective lateral ends of the master cylinder 22. The first slave cylinder 24 and the second slave cylinder 26 further contain hydraulic fluid and are fluidly coupled with the master cylinder 22 to allow for exchange of the hydraulic fluid therebetween. Each of the first slave cylinder 24 and the second slave cylinder 26 extend distally from the side wall of the master cylinder 22. Each of the first slave cylinder 24 and the second slave cylinder 26 also has a smaller diameter than the master cylinder 22 and may have an axial length longer than the axial length of the master cylinder 22, although this may be unnecessary. A fluid transfer cylinder 28 extends parallel to the master cylinder 22 and orthogonal to each of the first slave cylinder 24 and the second slave cylinder 26. The fluid transfer cylinder 28 is both mechanically connected with and fluidly coupled with each of the first slave cylinder 24 and the second slave cylinder 26 adjacent their distal ends.

A first slave piston 34 is disposed within the first slave cylinder 24. The first slave piston 34 engages the interior cylindrical wall of the first slave cylinder 24 to create a fluid-tight seal therewith and is adapted to travel axially within the first slave cylinder 24. Similarly, a second slave piston 36 is disposed within the second slave cylinder 26 and engages the interior cylindrical wall of the second slave cylinder 26 to create a fluid-tight seal therewith. The second slave piston 36 is adapted to travel within the second slave cylinder 26 along its axial length. A first steering cable 38 is connected with a distal side of the first slave piston 34. The first steering cable 38 extends distally from the first slave piston 34 and exits the distal end of the first slave cylinder 24 via an aperture within the distal end of the first slave cylinder 24. Similarly, a second steering cable 40 is connected with a distal side of the second slave piston 36. The second steering cable 40 extends distally from the second slave piston 36 and exists the second slave cylinder 26 through an aperture within the distal end of the second slave cylinder 26. Each of the apertures in the distal ends of each of the first and second slave cylinders 24, 26 is provided with a sealing member, for example, an O-ring, that seals around each of the first steering cable 38 and second steering cable 40, respectively, to insure that none of the fluid within the first and second slave cylinders 24, 26 leaks through the apertures.

An actuator channel 20 is formed in the wall of the pivot actuator 18 at the apex of the tear-drop shape. The first steering cable 38 and the second steering cable 40 extend distally from the first slave cylinder 24 and the second slave cylinder 26, respectively, to exit the chamber 19 formed by the pivot actuator 18 through the actuator channel 20. Within the chamber 19 of the pivot actuator 18, the first and second steering cables 38, 40 are guided around proximal lateral guiding pins 46, a center guiding pin 48, and distal lateral guiding pins 50 in order to prevent the entanglement of and maintain an appropriate separation distance between the first steering cable 38 and the second steering cable 40. The pivot actuator 18 is pivotally mounted to the handle base 10 via a pivot pin 44 connected at a first end to the bottom actuator panel 56 and at an opposite end to the handle base 10 in the handle bay area 12. The pivot pin 44 is positioned in the bottom actuator panel 56 distally at the apex of the tear-drop shape of the pivot actuator 18.

The master cylinder 22 is also pivotally mounted to the handle base 10 via a cylinder fastener 42. The cylinder fastener 42 is affixed around the master cylinder 22 equidistant from the lateral ends of the master cylinder 22. A tab on the distal side of the cylinder fastener 42 has a fastener pin 65 which extends through an arcuate slot 60 within the bottom actuator panel 56 and is pivotally mounted to the handle base 10 within the area of the handle bay 12. Thus, the cylinder fastener 42 connects a proximal area of the bottom actuator panel 56 to the handle base 10 via the interface between the cylinder fastener 42 and the top side of the bottom actuator panel 56. The bottom actuator panel 56, and thus the pivot actuator 18, are able to move back and forth laterally as the pivot actuator 18 is pivoted about the pivot pin 44 (as described in greater detail below) because the actuator panel slot 60 in the bottom actuator panel 56 allows the bottom actuator panel 56 to slide past fastening pin 43 of the cylinder fastener 42.

FIGS. 1 and 2 further depict a plurality of lead wires 52 entering a wire sheath 62 disposed within a proximal handle channel 14 within the handle base 10. Connector plugs 54 are provided on the proximal ends of the plurality of lead wires 52 for connecting the lead wires 52 within the various systems used in cardiac catheterization treatments, for example, a radio frequency energy generator for ablation, a cardiac sensing and mapping system, or both. The plurality lead wires 52 is directed through a wire sheath 62 into a passageway within the handle base 10 (not shown) whereby the lead wires 52 can travel through the handle base 10 underneath the handle bay 12 and the pivot actuator 18, and related components housed therein. The lead wires 52 emerge beyond the distal end of the handle bay 12 within the actuator handle 6 and are trained through the catheter shaft 4 which is disposed within a proximal handle channel 14 before exiting the actuator handle 6 distally. Once the first and second steering cables 38,40 exit the chamber 19 through the actuator channel 20, the first and second steering cables 38,40 are similarly trained through the catheter shaft 4 within the distal handle channel 16 of the handle base 10. The plurality of lead wires 52 and the first and second steering cables 38,40 then extend within the catheter shaft 4 until they terminate within an ablation tip 64 at the distal end of the catheter shaft 4 (see FIG. 5).

Figure 4A:
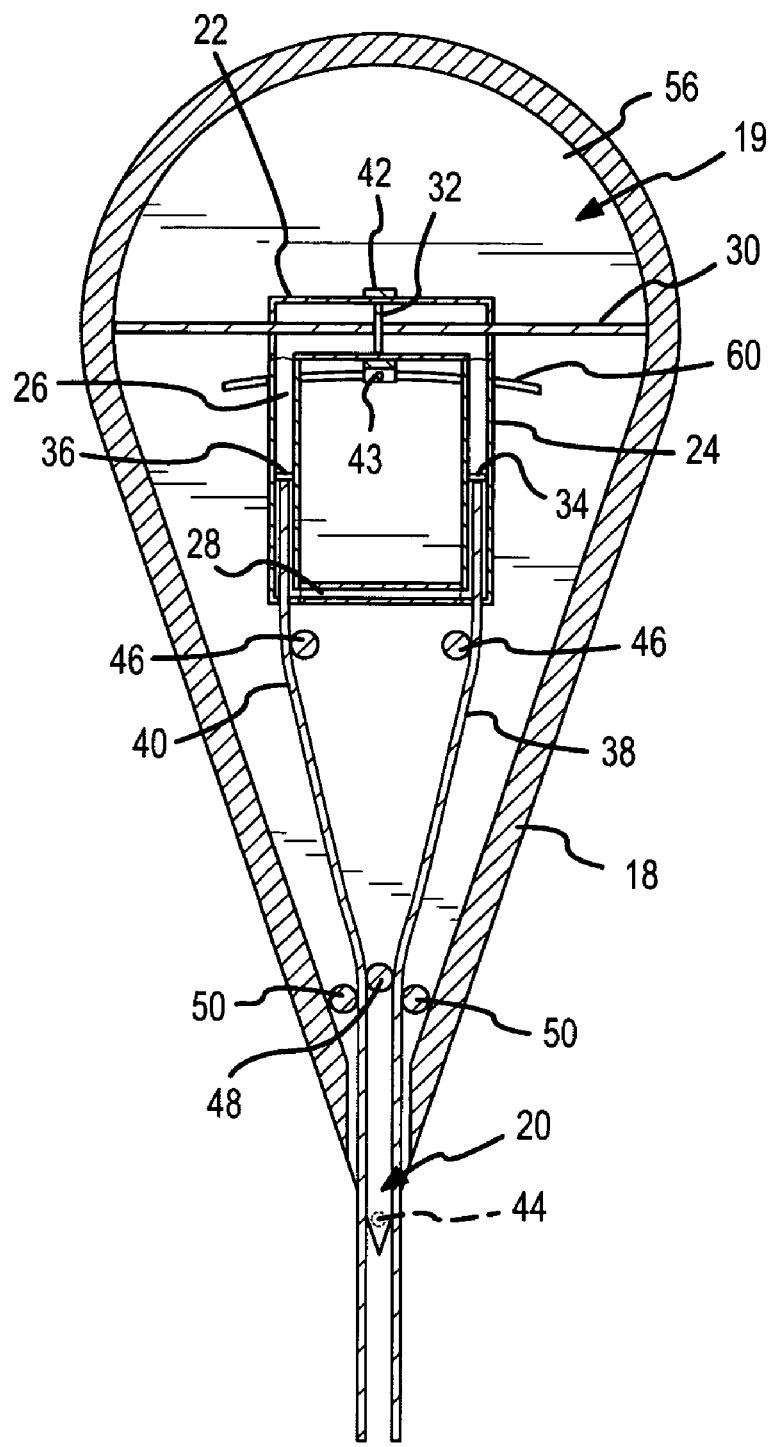
FIG. 4a is a top plan view, in cross-section, of the pivot actuator and hydraulic components of FIG. 3 in an equilibrium position.

FIGS. 4A-4C and 5 depict alternate positions for displacement of the pivot actuator 18 and the consequent effect on the ablation tip 64 of the catheter shaft 4. FIG. 4A depicts the pivot actuator 18 at an equilibrium position. In this position, the master piston 32 is positioned within the middle of the master cylinder 22 equidistant from each lateral end of the maser cylinder 22. Similarly, each of the first slave piston 34 and the second slave piston 36 is positioned at a corresponding axial location within the first slave cylinder 24 and the second slave cylinder 26, respectively. The first steering cable 38 is the same length as the length of the second steering cable 40. In this equilibrium position therefore, the tensile force exerted on the ablation tip 64 by each of the first steering cable 38 and the second steering cable 40 at a termination point 65 within the ablation tip 64 is equal and the ablation tip 64 maintains a generally straight orientation.

Figures 4B, 4C:
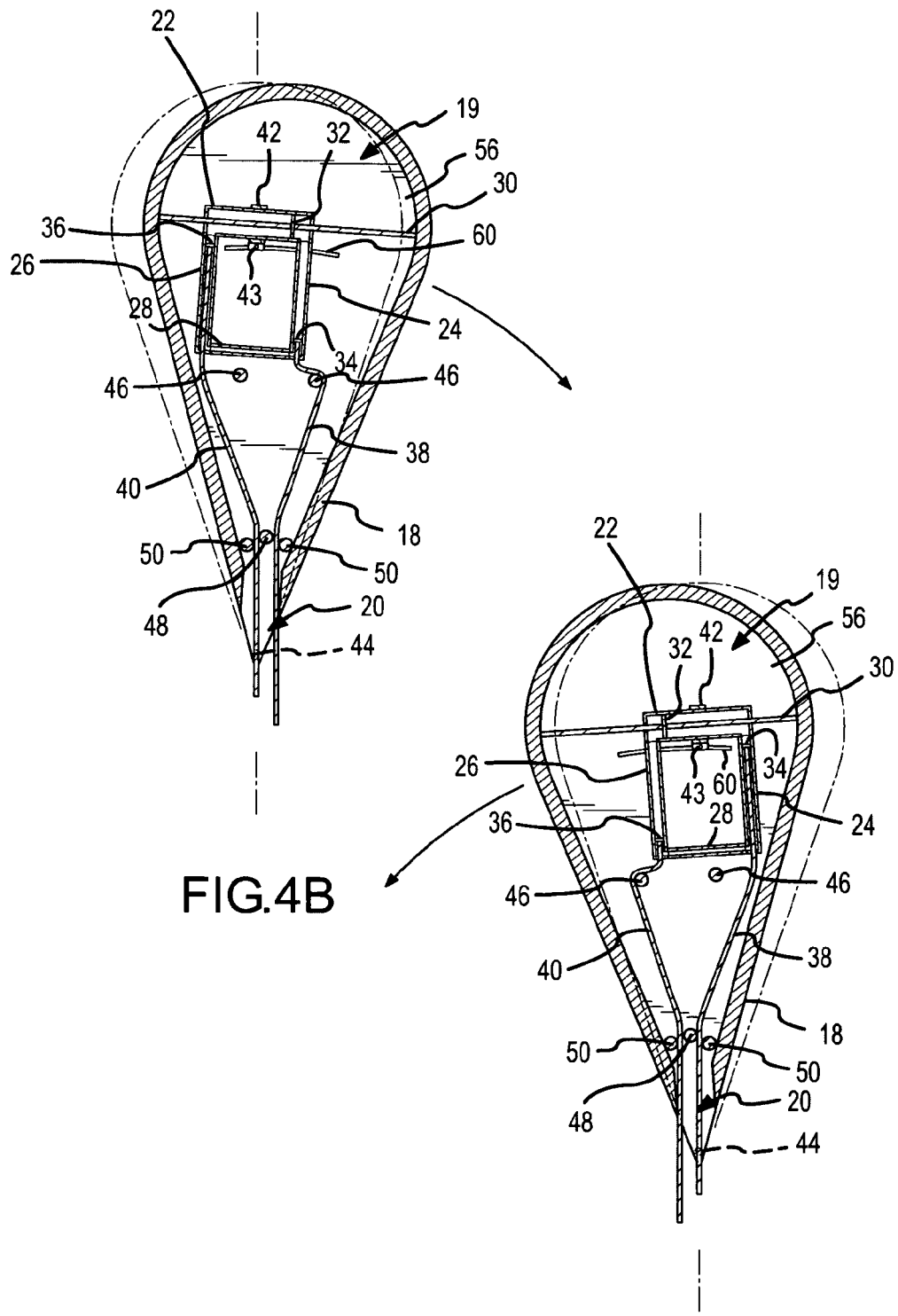
FIG. 4b is a top plan view in cross-section of the pivot actuator and hydraulic components of FIG. 3 in a first displaced position.
FIG. 4c is a top plan view in cross-section of the pivot actuator and hydraulic components of FIG. 3 in a second displaced position.

Optionally, as shown in FIG. 4B, the pivot actuator 18 may be pushed in a lateral, rightward direction by a clinician operating the actuator assembly 2. By displacing the pivot actuator 18 to the right, the master piston 32, which is affixed to the master shaft 30, is caused to move axially rightward within the master cylinder 22. The master cylinder 22, which is pivotally mounted to the handle base 10 by the cylinder fastener 42 and the fastener pin 43, remains in a laterally fixed positioned relative to the handle base 10. Therefore, the pivot actuator 18 moves laterally rightward with respect to stationary master cylinder 22.

Movement of the master piston 32 within the master cylinder 22 causes pressure on the fluid within the right lateral half of the master cylinder 22, thereby forcing fluid out of the master cylinder 22 into the first slave cylinder 24. The fluid forced into the first slave cylinder 24 causes pressure against the first slave piston 34, which forces the first slave piston 34, and therefore the attached first steering cable 38, to move distally along the axis of the first slave cylinder 24. Fluid in the first slave cylinder 24 that was distal to the first slave piston 34 is similarly forced out of the first slave cylinder 24 and into the fluid transfer cylinder 28. Fluid originally residing in the fluid transfer cylinder 28 is thereby forced into the second slave cylinder 26, which forces the second slave piston 36 to move proximally along the axis of the second slave cylinder 26. As the second steering cable 40 is attached to the distal side of the second slave piston 36, the second steering cable 40 is pulled proximally by the movement of the second slave piston 36. Finally, the fluid that was proximal to the second slave piston 36 within the second slave cylinder 26 flows into the master cylinder 22 on the left lateral side of the master piston 32. The fluid movement from the second slave cylinder 26 fills the potential fluid void on the left lateral side of the master piston 32 due to the rightward lateral movement of the master piston 32 within the master cylinder 22.

Figure 5:
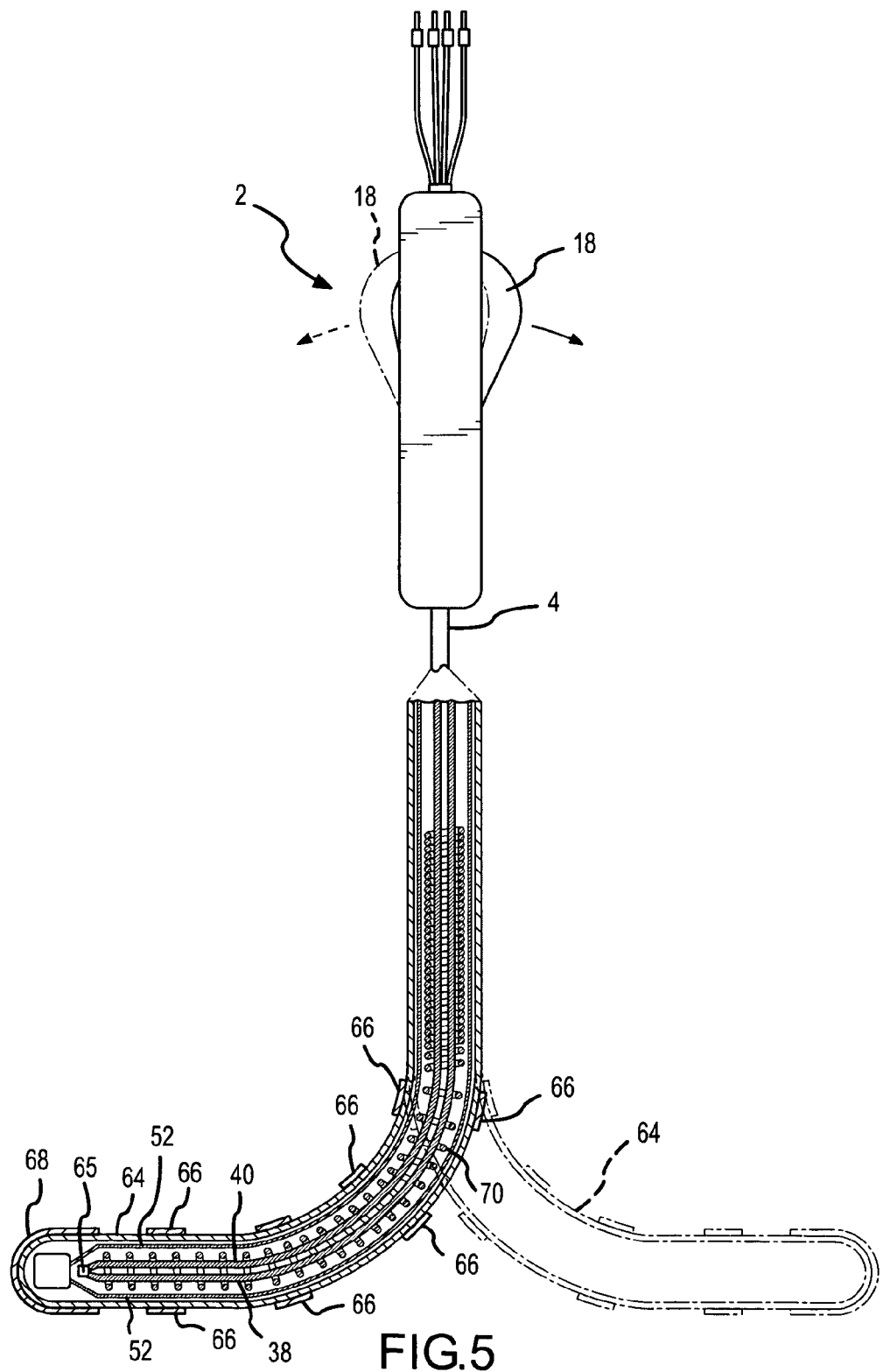
FIG. 5 is a top plan view of the actuator assembly of FIG. 1 with the ablation tip of the attached catheter enlarged and in cross-section. The intermediate section of the catheter is not shown. The ablation tip is shown in a deflected position corresponding to the displacement of the actuator. The ablation tip is further shown in phantom in an alternate deflected position corresponding to the alternate displacement of the actuator, also shown in phantom.

FIG. 5 depicts a typical ablation tip 64 that may form the end of the catheter shaft 4 extending distally from the actuator assembly 2. The ablation tip 64 may be covered by a series of ring electrodes 66 forming bands around the outer surface of a catheter shaft 4. The distal end of the ablation tip 64 may be further capped by a tip electrode 68. The lead wires 52 may be variously connected to the ring electrodes 66 or the tip electrode 68, or any other sensors or electrodes disposed on the ablation tip 64. The ablation tip 64 of the catheter shaft 4 may further house a helical coil 70 to help provide structural integrity to the ablation tip 64 as it is deflected in different directions. The coil 70 may further act as an equilibrium force to return the ablation tip 64 to a "straight" orientation after the ablation tip 64 has been deflected in a particular direction.

When the second steering cable 40 is moved proximally by the fluid force exerted on the second slave piston 36 as in FIG. 4B, increased tensile force is placed on the termination point 65 in the ablation tip 64 by the second steering cable 40. This increased tensile force by the second steering cable 40 causes the ablation tip 64 to bend proximally and laterally leftward as shown in FIG. 5. As noted, when the pivot actuator 18 is displaced rightward, the first steering cable 38 is pushed distally out of the first slave cylinder 24. This creates slack in the first steering cable 38 and therefore reduced tensile force on the termination point 65 in the ablation tip 64 attributed to the first steering cable 38. This slack in the first steering cable 38 encourages the directional bending of the ablation tip 64 and allows the first steering cable 38 to assume a larger outside radius of curvature within the ablation tip 64 as shown in FIG. 5 as compared to the radius of curvature of the second steering cable 40.

As shown in FIG. 4C, when the pivot actuator 18 is displaced laterally in a leftward direction from the equilibrium position within the handle bay 12 of the actuator handle 6, the master piston 32, which is affixed to the actual mid-point of the master shaft 30, moves laterally leftward within master cylinder 22. This relative movement between the master piston 32 and the master cylinder 22 forces fluid in the left lateral section of the master cylinder 22 to flow into the second slave cylinder 26. This fluid flow into the second slave cylinder 26 forces the second slave piston 36 to travel distally along the axis of the second slave cylinder 26. Because the second steering cable 40 is affixed to the second slave piston 36, the second steering cable 40 is likewise moved distally. This reduces the tensile force exerted by the second steering cable 40 on the termination point 65 in the ablation tip 64. Fluid within the second slave cylinder 26 on the distal side of the second slave piston 36 is forced from the second slave cylinder 26 into the fluid transfer cylinder 28. The fluid in the fluid transfer cylinder 28 is forced into the first slave cylinder 24. This fluid movement within the first slave cylinder 24 creates fluid pressure on the distal side of the first slave piston 34 and forces the first slave piston 34 proximally within the first slave cylinder 24.

Because the first steering cable 38 is affixed to the distal side of the first slave piston 34, the first steering cable 38 is pulled proximally along the axis of the first slave cylinder 24. This increases the tensile force exerted by the first steering cable 38 on the termination point 65 within the ablation tip 64. The increased tensile force causes the ablation tip 64 to deflect proximally and laterally rightward as shown in phantom in FIG. 5. Because of the reduced tensile force on the second steering cable 40 and the slack created therein, the second steering cable 40 may assume a greater radius of curvature within the ablation tip 64 as the ablation tip 64 is deflected proximally rightward and thus does not impede the deflection of the ablation tip 64.

As indicated in FIG. 4C, the fluid in the first slave cylinder 24 proximal to the first slave piston 34 is forced to the right lateral side of the master cylinder 22. Fluid fills the excess volume with the master cylinder 22 created as the master piston 32 moves laterally leftward within the master cylinder 22. By transferring fluid between the cylinders, an equal fluid pressure on each side of each of the pistons 32, 34, 36 is ultimately maintained within the hydraulic system. This establishes a general hydraulic equilibrium which tends to hold the pivot actuator 18 in a particular displacement position to which it is pushed by a clinician. This in turn tends to maintain the ablation tip 64 in a deflected position once it is deflected. As previously noted in the description of FIG. 5, the ablation tip 64 may be provided with a structural component, for example, the coil 70, which tends to exert a normalizing force on the ablation tip 64 to return the ablation tip 64 from a deflected position to a generally straight position. The effect of such a normalizing force is to some extent dampened by the hydraulic system of the present invention due to the equal hydraulic pressure maintained on each side of each of the pistons 32, 34, 36. Therefore, although the ablation tip 64 will ultimately return to a straight position if the clinician releases actuation pressure on the pivot actuator 18, the return of the ablation tip 64 from a deflected state will occur gradually due to the dampening effect of the hydraulic system.

It should be noted that when the pivot actuator 18 is displaced laterally in order to deflect the ablation tip 64 of catheter shaft 4, the fastener pin 43 of the cylinder fastener 42, while pivotally mounted to the handle base 10 by the pivot pin 44, slides within the actuator panel slot 60 of the bottom actuator panel 56. This design maintains the master cylinder 22 in a fixed lateral position with respect to the handle base 10, while allowing the master piston 32 to move laterally with respect to the master cylinder 22 and accommodate the arcuate nature of the lateral movement of the pivot actuator 18. Because the master shaft 30 is fixedly mounted to the walls of the pivot actuator 18, the master shaft 30 actually changes its angle of orientation from a relative horizontal orientation when pivot actuator 18 is in an equilibrium position. The design of the cylinder fastener 42 accounts for the angular change of the master shaft 30 by additionally pivoting about the fastener pin 43. The fastener pin 43 of the cylinder fastener 42, therefore allows the master cylinder 22 to maintain a coaxial relationship with the master shaft 30 as the pivot actuator 18 moves laterally back and forth.

It should also be noted that the diameter of the master cylinder 22 is greater than the diameters of each of the first and second slave cylinders 24, 26, respectively. Because of this, a slight deflection of the pivot actuator 18 causes a large volume of fluid to flow into and out of the first and second slave cylinders 24, 26. This translates into a long travel distance for each of the first and second slave pistons 34, 36 within the first and second slave cylinders 24, 26 with a minimal movement of the pivot actuator 18. The large diameter of the master cylinder 22 and the consequent large fluid volume provides greater deflection and control of the ablation tip 64 by a clinician with a smaller displacement of the pivot actuator 18.

Figure 6:
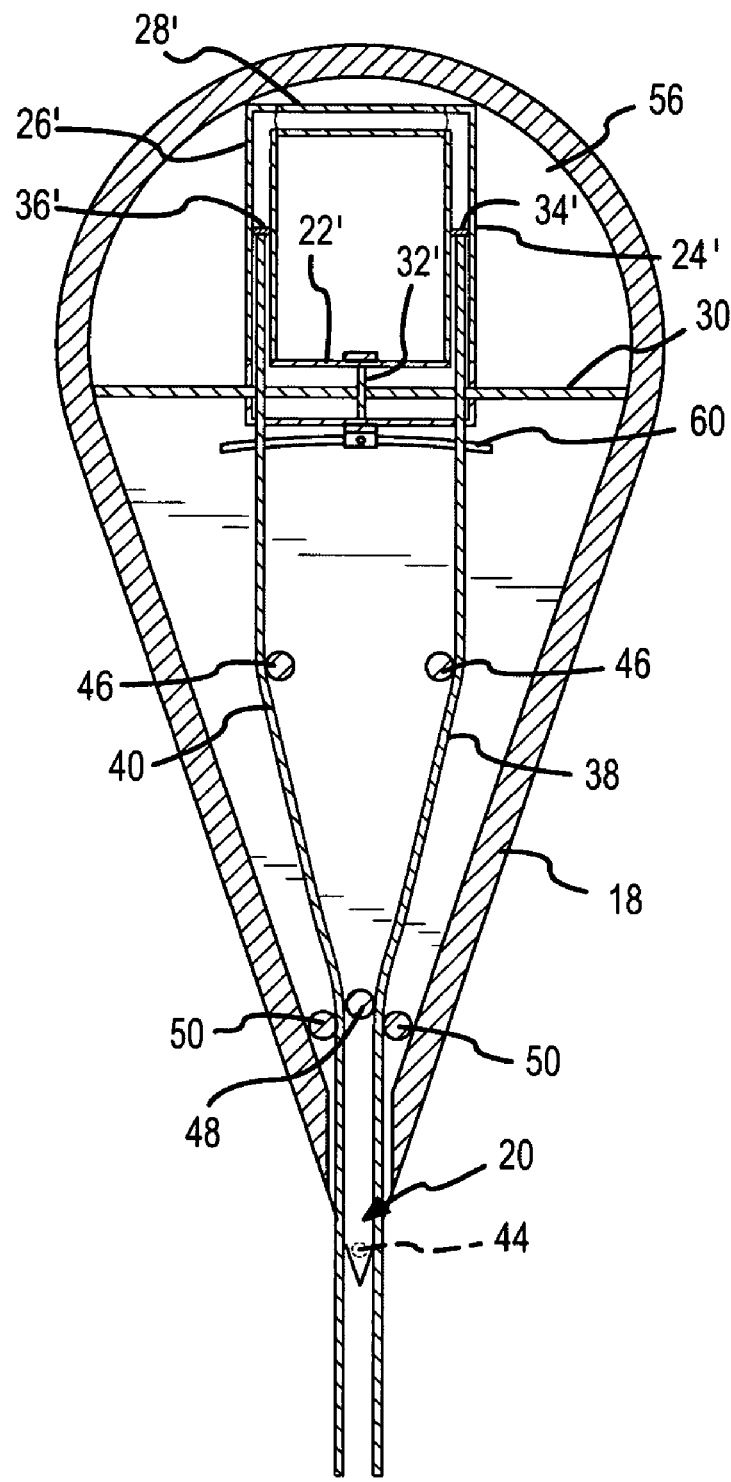
FIG. 6 is a top plan view in cross-section of an alternate embodiment of the pivot actuator and hydraulic components of the actuator assembly of FIG. 1.

FIG. 6 depicts an alternative embodiment of the hydraulic system for the actuator assembly of FIG. 1. In FIG. 6, the master cylinder 22' is mounted within the chamber defined by the pivot actuator 18 by the cylinder fastener 42 as previously described. However, in this embodiment each of first and second slave cylinders 24', 26' extends orthogonally from the lateral ends of the master cylinder 22' in a direction distal from the master cylinder 22. The fluid transfer cylinder 28' is positioned between the proximal ends of the first and second slave cylinders 24', 26'. In this embodiment, the first and second steering cables 38, 40 extend distally from their respective attachment points with the first and second slave pistons 34', 36' through apertures within the cylindrical sidewall of the master cylinder 22 adjacent each lateral end of the master cylinder 22, respectively.

The hydraulic operation in this alternative embodiment is generally the same as the hydraulic operation of the first embodiment with one exception. In this embodiment, the deflection of the ablation tip 64 curves in the same lateral direction as the lateral displacement of the pivot actuator 18, whereas in the first embodiment, the lateral direction of the deflection of the ablation tip was in a direction opposite to lateral displacement of the pivot actuator. For example, in the embodiment of FIG. 6 if the pivot actuator 18 is pushed laterally leftward, the second slave piston 36' will be caused to move proximally within the second slave cylinder 26, thereby exerting increased tensile force on the second steering cable 40 and thus causing a proximal and leftward deflection of the ablation tip 64.

Figure 7:
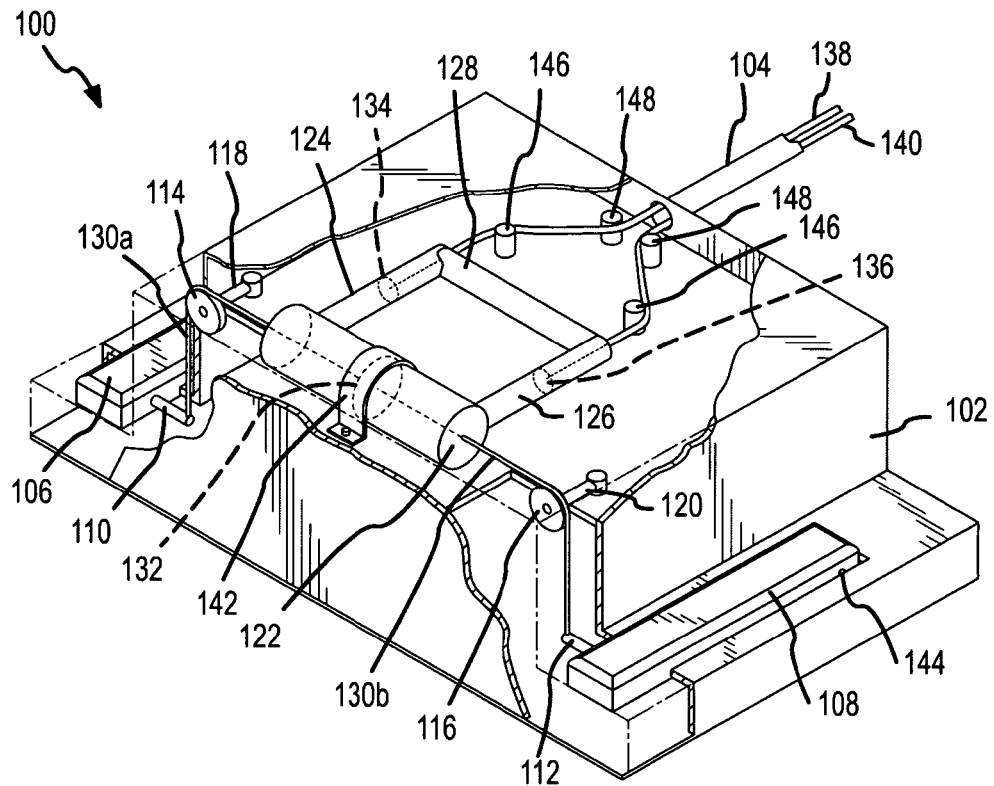
FIG. 7 is an isometric view on partial cut-away of a foot pedal actuator according to another embodiment of the invention.
Figure 8:
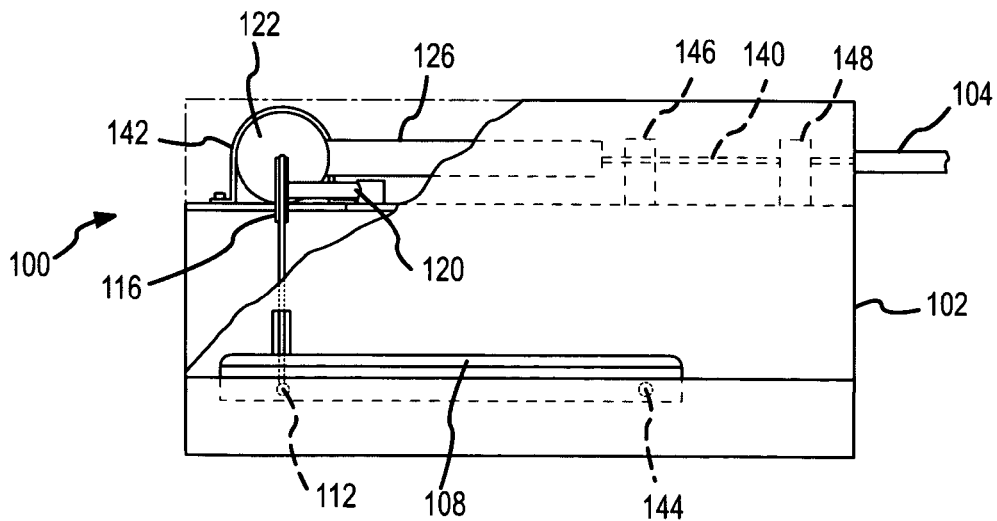
FIG. 8 is a right side elevation view in partial cut-away of the foot pedal actuator of FIG. 7.

FIGS. 7-9C depict another embodiment of the present invention in the form of a foot pedal actuator 100. The foot pedal actuator 100 may be desirable for use by a clinician because it allows the clinician to control the deflection of the ablation tip 64 with the clinician's feet while freeing the clinician's hands to perform other functions during the procedure. As shown in FIGS. 7 and 8, the foot pedal actuator 100 includes a similar hydraulic system to the actuator assembly of FIG. 1. However, the actuator linkage is somewhat different than in FIG. 1.

As shown in FIG. 7, a foot pedal case 102 houses the hydraulic system and supports a left foot pedal 106 and a right foot pedal 108 on either side of the hydraulic system. The left foot pedal 106 is attached to the foot pedal case 102 at an end opposite the left linkage member 110 by a foot pedal hinge 144, which allows the proximal end of the left foot pedal 106 to move in a vertical orientation. A left linkage member 110 protrudes from a right interior side of the left foot pedal 106. The left linkage member 110 is connected with a left master shaft cable 130*a*, which is connected at an opposite end to the left lateral side of the master piston 132 within the master cylinder 122. As indicated, the left foot pedal 106 is positioned within a plane lower than the plane of the hydraulic system. The master cylinder 122 is fixedly mounted to a platform in the foot pedal case 102 by the cylinder fastener 142. The left master shaft cable 130*a* therefore extends around a left pulley 114 attached to the foot pedal case 102 by a left pulley support 118. The left pulley 114 translates the vertical movement of the left master shaft cable 130*a* imparted by the left foot pedal 106 into lateral movement to displace the master piston 132 within the master cylinder 122.

Similarly, the right foot pedal 108 is attached to the foot pedal case 102 at an end opposite the right linkage member 112 by a foot pedal hinge 144, which allows the proximal end of the right foot pedal 108 to move in a vertical orientation. A right linkage member 112 extends from the left interior side of the right foot pedal 108. The right linkage member 112 is connected with a right master shaft cable 130*b*, the opposite end of which is connected with the right lateral side of the master piston 132 within the master cylinder 122. In order to translate the vertical movement of the right foot pedal 108 to the master piston 132, the right master shaft cable 130*b* travels over a right pulley 116 mounted to the foot pedal case 102 by a right pulley support 120. The right pulley 116 translates the right master shaft cable 130*b* into a horizontal orientation. As in the earlier embodiments, the left master shaft cable 130*a* and the right master shaft cable 130*b* each extend through apertures within the lateral ends of the master cylinder 122. Sealing members are provided about the apertures in the lateral ends of the master cylinder 122 and seal against the right and left master shaft cables 130*a*, 130*b* to prevent fluid linkage out of the master cylinder 122.

As in the previous embodiments, the first slave cylinder 124 and the second slave cylinder 126 are each respectively physically and fluidly coupled with the master cylinder 122. Each of the first and second slave cylinders 124, 126 extends orthogonally from a side wall of the master cylinder 122 in a distal orientation. A first slave piston 134 connected with the proximal end of the first steering cable 138 resides within the first slave cylinder 124. Similarly, a second slave piston 136 connected with the proximal end of a second steering cable 140 resides within the second slave cylinder 126. A fluid transfer cylinder 128 is physically and fluidly coupled with each of the first and second slave cylinders 124, 126 and extends orthogonally between the first and second slave cylinders 124, 126 adjacent their distal ends.

The first steering cable 138 and the second steering cable 140 each immerge through respective apertures in the distal ends of the first and second slave cylinders 124, 126, respectively. The first and second steering cables 138, 140 are guided within the foot pedal case 102 by proximal lateral guiding pins 146 and distal lateral guiding pins 148 to prevent entanglement of and maintain an appropriate separation distance between each of the first and second steering cables 130,140. The first and second steering cables 138, 140 exit the foot pedal case 102 through an aperture that is connected with a cable sheath 104 through which the first and second steering cables 138,140 are trained.

Figure 9A:
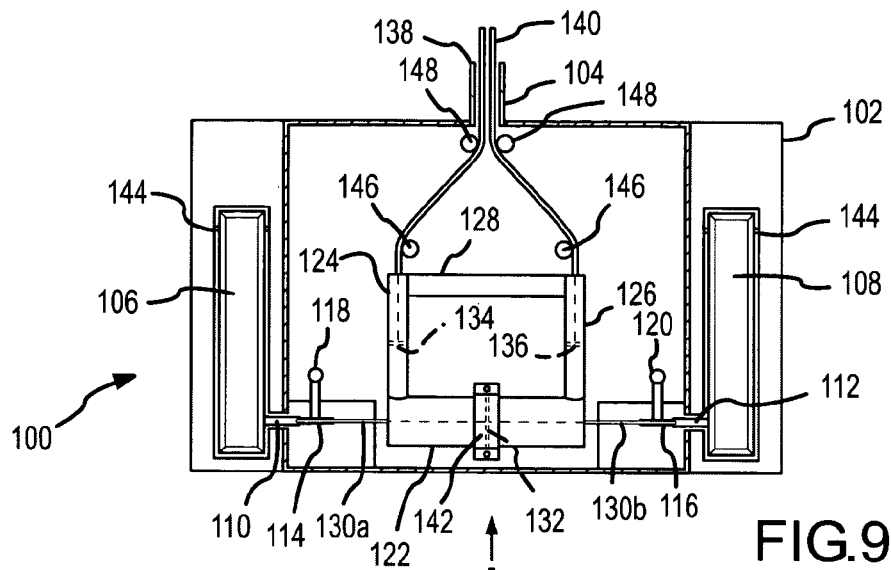
FIG. 9A is a top plan view in partial cross-section of the foot pedal actuator of FIG. 7 in an equilibrium position.
Figure 9B:
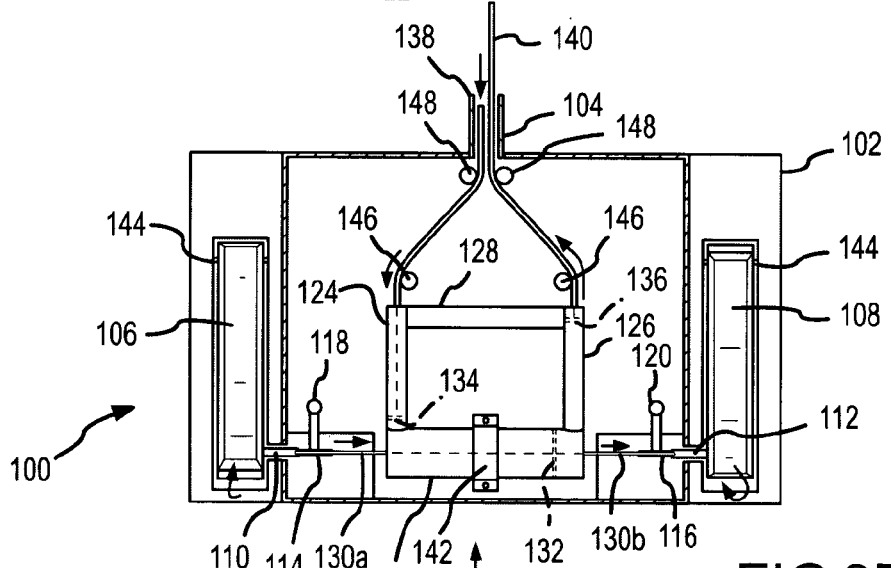
FIG. 9B is a top plan view in partial cross-section of the foot pedal actuator of FIG. 7 in a first displaced position with the right foot pedal depressed.
Figure 9C:
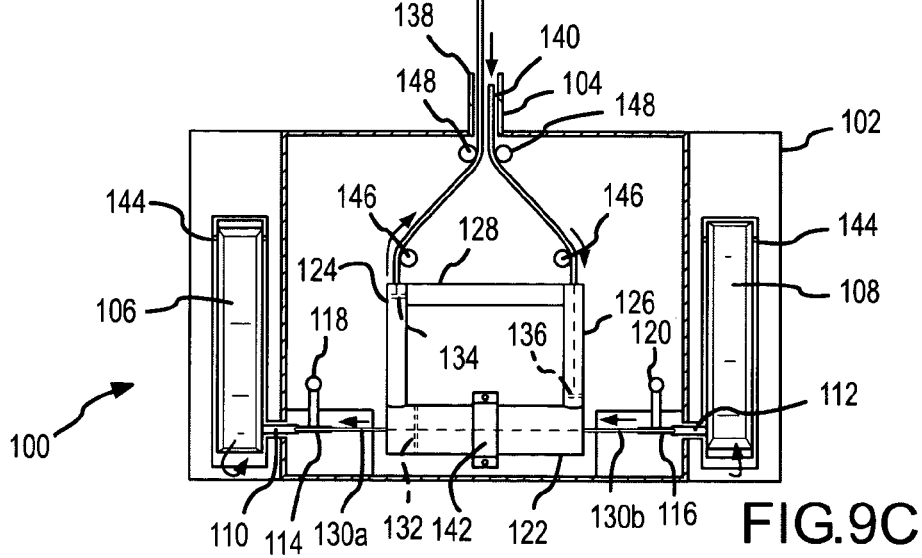
FIG. 9C is a top plan view in partial cross-section of the foot pedal actuator of FIG. 7 in a first displaced position with the left foot pedal depressed.

As shown in FIGS. 9A-9C, the operation of the foot pedal actuator 100 is similar to the operation of the actuator assembly with the pivot actuator of FIG. 1. FIG. 9A depicts the foot pedal actuator 100 in an equilibrium position, wherein the left and right foot pedals 106, 108 are not displaced from a level horizontal position, the master piston 132 is positioned in the center of the master cylinder 122 equidistant from the lateral ends of the master cylinder 122, and each of the first slave piston 134 and the second slave piston 136 is in a comparable axial position within each of the first slave cylinder 124 and the second slave cylinder 126, respectively. As depicted in FIG. 9B, the right foot pedal 108 is displaced downward. This displacement increases the tension on the right master shaft cable 130*b*, which is pulled downward by the right linkage member 112. The right pulley 116 translates this downward vertical movement of the right master shaft cable 130*b* into a rightward horizontal movement that pulls the master piston 132 rightward within the master cylinder 122. The rightward movement of the right master shaft cable 130*b* similarly pulls the left master shaft cable 130*a* in a rightward direction, thus raising the proximal end of the left foot pedal 106.

The movement of the master piston 132 forces fluid in the right half of the master cylinder 122 into the second slave cylinder 126, thus forcing the second slave piston 136 to move distally along the axis of the second slave cylinder 126. Fluid in the second slave cylinder 126 is forced into the fluid transfer cylinder 128 and, in turn, fluid in the fluid transfer cylinder 128 is forced into the first slave cylinder 124. This causes the first slave piston 134 to travel proximally within the first slave cylinder 124, thereby creating increased tensile force on the first steering cable 138 and causing a leftward deflection of the ablation tip at the end of an attached catheter.

Alternatively, as shown in FIG. 9C, when the left foot pedal 106 is depressed downwardly, the left master shaft cable 130*a* attached to the left linkage member 110 is pulled in a downward vertical direction. This downward vertical movement of the left master shaft cable 130a is translated by the left pulley 114 into leftward lateral movement of the left master shaft cable 130a, thereby pulling the master piston 132 axially leftward within the master cylinder 122. The leftward lateral movement of the master piston 132 forces fluid out of the master cylinder 122 into the first slave cylinder 124, thereby forcing the first slave piston 134 distally along the axis of the first slave cylinder. This displacement of the first slave piston 134 decreases the tensile force on the first steering cable 138. As before, fluid from the first slave cylinder 124 is forced into the fluid transfer cylinder 128, and fluid from the fluid transfer cylinder 128 is similarly forced into the second slave cylinder 126. The fluid pressure on the second slave cylinder 126 causes the second slave piston 136 to move proximally along the axis of the second slave cylinder 126. Because the second steering cable 140 is attached to the second slave piston 136, the second steering cable 140 is pulled in a proximal direction, thereby increasing the tensile force on the ablation tip of the attached catheter and deflecting the ablation tip in a rightward direction.

Figure 10:
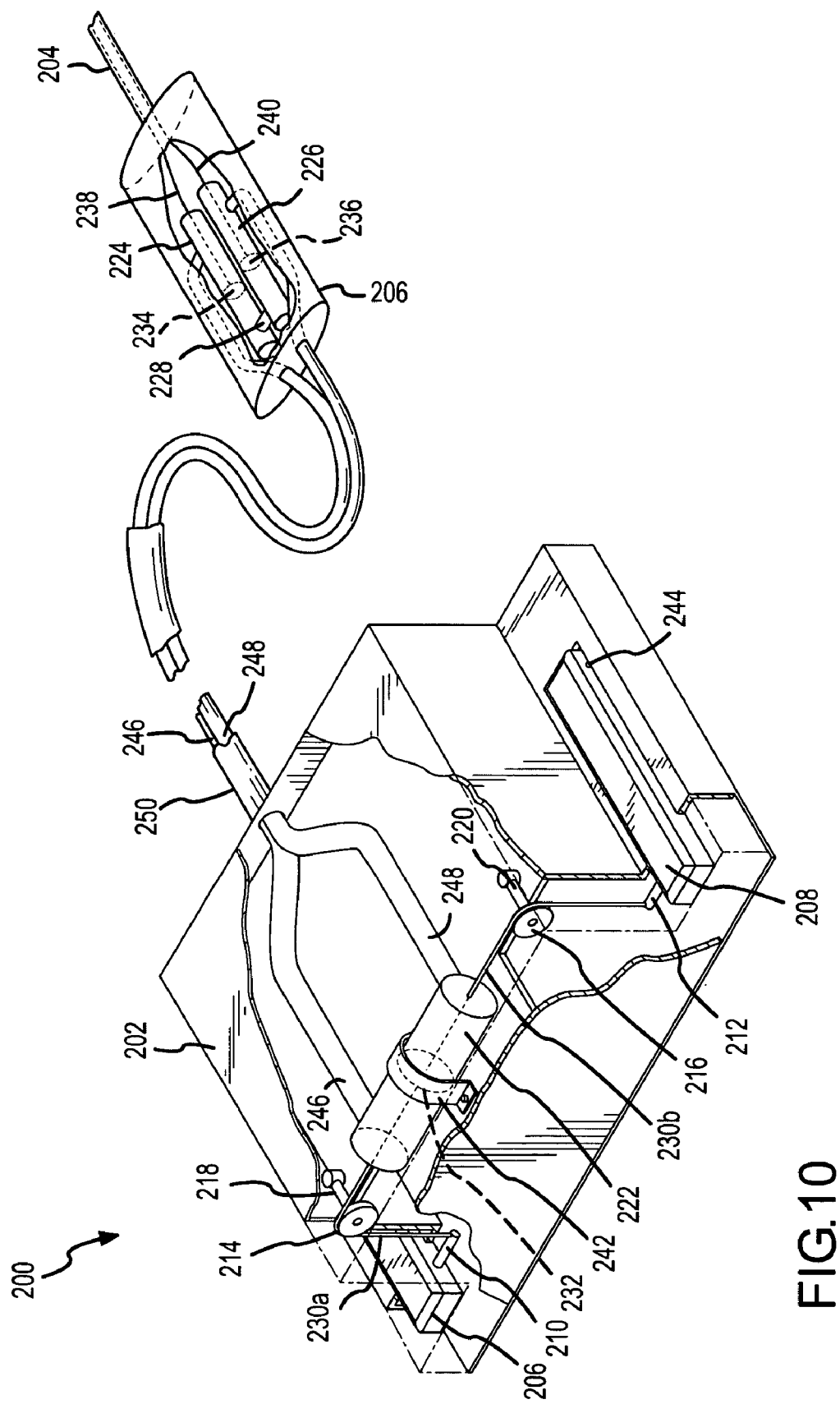
FIG. 10 is an isometric view in partial cut-away of a pneumatic foot pedal actuator according to an alternate embodiment of the invention.

In FIG. 10 an alternative embodiment of a foot pedal actuator 200 is depicted. In this embodiment, either a pneumatic or hydraulic actuation system is contemplated. The pneumatic/hydraulic foot pedal actuator 200 of FIG. 10 is similar to the foot pedal actuator of FIG. 7, except that the first and second slave cylinders 224, 226 are positioned in a handle 206 and linked to the foot pedal actuator 200 by first and second tubes 246, 248, respectively. As the left and right foot pedals 206, 208 are depressed, the left and right master shaft cables 230a, 230b move the master piston 232 laterally within the master cylinder 222. In a pneumatic embodiment, the movement of the master piston 232 compresses air in front of the master piston 232 in the direction of movement and creates a vacuum pressure behind master piston 232 opposite the direction of movement. In a hydraulic embodiment, the movement of the master piston 232 increases the fluid pressure of the fluid in front of the master piston 232 in the direction of movement and decreases the fluid pressure behind master piston 232 opposite the direction of movement. The lateral ends of the master cylinder 222 are physically and fluidly coupled with the first slave cylinder 224 and the second slave cylinder 226 via the first tube 246 and the second tube 248. A first slave piston 234 is positioned within the first slave cylinder 224. Similarly, a second slave piston 236 is positioned within the second slave cylinder 226. The first and second tubes 246, 248 may be encased in a sheathing 250 for protection and to prevent entanglement.

In contrast to the embodiments previously described, the first slave cylinder 224 and the second slave cylinder 226 are not connected directly to the master cylinder 222. The first and second slave cylinders 224, 226 are in fluid communication with the master cylinder 222 via the first and second tubes 246, 248, which are fluidly coupled to the distal ends of the first and second slave cylinders 224, 226, respectively. The proximal ends of the first and second slave cylinders 224, 226 are fluidly connected at their proximal ends by a fluid transfer cylinder 228. In a pneumatic embodiment, when the left foot pedal 206 is depressed, the master piston 232 is pulled leftward within the master cylinder 222 and compresses the air within the leftward section of the master cylinder 222. This forces air into the first tube 246 and ultimately into the first slave cylinder 224. Because of the smaller diameter of the first slave cylinder 224 compared to the diameter of the master cylinder 222, a small movement of the master piston 232 forces a large volume of air into the first tube 246 and the first slave cylinder 224. This influx of air increases the air pressure within the first slave cylinder 224 to push the first slave piston 234 proximally a greater linear distance than the movement of the master piston 232. The movement of the first slave piston 234 pulls the first steering cable 238 to ultimately deflect the ablation tip at the distal of the catheter 204 in a first direction. Air in the first slave cylinder 224 on the proximal side of the first slave piston 234 is forced through the fluid transfer cylinder 228 into the proximal end of the second slave cylinder 226, thereby forcing the second slave piston 236 distally and relaxing any tension that may have been previously placed on the second steering cable 240.

Similarly when the right foot pedal 208 is depressed in a pneumatic embodiment, the master piston 232 is pulled rightward within the master cylinder 222 and compresses the air within the rightward section of the master cylinder 222. This forces air into the second tube 248 and ultimately into the second slave cylinder 226. Because of the smaller diameter of the second slave cylinder 226 compared to the diameter of the master cylinder 222, a small movement of the master piston 232 forces a large volume of air into the second tube 248 and the second slave cylinder 226. This influx of air increases the air pressure within the second slave cylinder 226 to push the second slave piston 236 proximally a greater linear distance than the movement of the master piston 232. The movement of the first slave piston 234 pulls the second steering cable 240 to ultimately deflect the ablation tip at the distal of the catheter 204 in a second direction. Air in the second slave cylinder 226 on the proximal side of the second slave piston 236 is forced through the fluid transfer cylinder 228 into the proximal end of the first slave cylinder 224, thereby forcing the first slave piston 234 distally and relaxing any tension that may have been previously placed on the first steering cable 238. It should be apparent that a pneumatic control of the type depicted in FIG. 10 could also be incorporated into a hand held actuator assembly, for example, of any of the types similar to FIGS. 1-6 and 11-15 rather than the foot pedal actuator of FIG. 10.

Alternately, the actuator of FIG. 10 may be controlled hydraulically rather than pneumatically. In this embodiment, the movement of the master piston 232 in the master cylinder 222 creates increased fluid pressure on a noncompressible fluid in either the first tube 246 or the second tube 248, depending upon the direction of movement of the master piston 232, and ultimately increases fluid pressure in either the first and second slave cylinder 224, 226, respectively. Increased fluid pressure in the first or second slave cylinder 224, 226 causes either the first slave piston 234 or the second slave piston 236 to move proximally, which pulls either the first or second steering cable 240, respectively, to ultimately deflect the ablation tip at the distal of the catheter 204.

Figure 11:
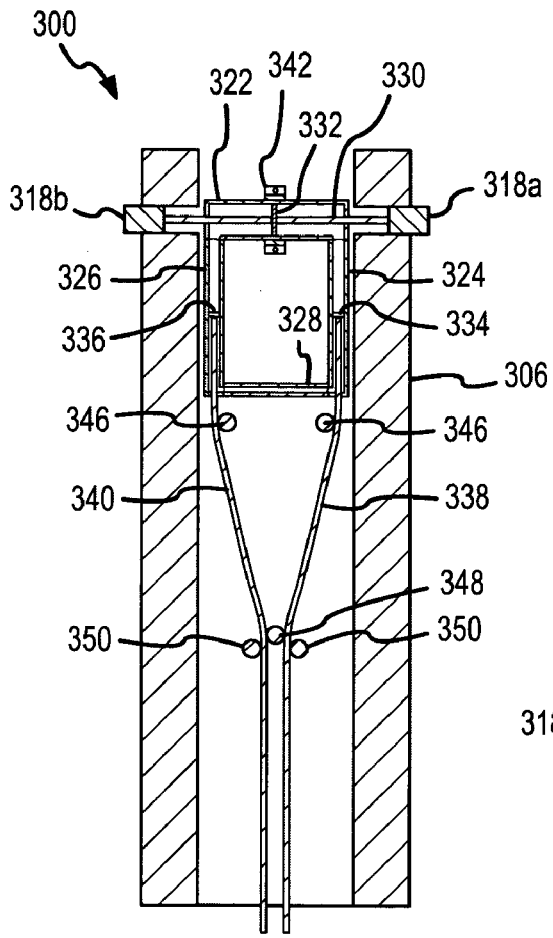
FIG. 11 is a top plan view in cross-section of an alternate embodiment of the present invention incorporating a toggle switch actuator assembly in an equilibrium position.
Figure 12:
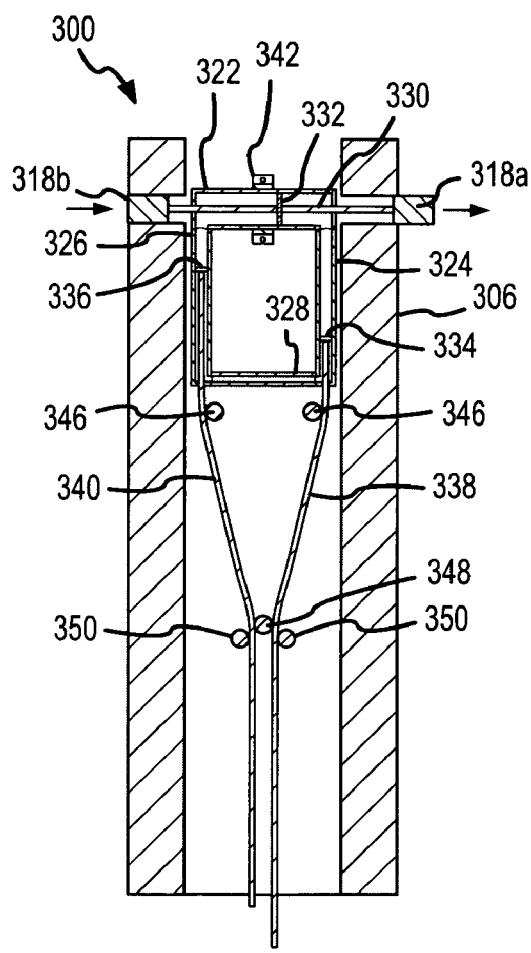
FIG. 12 is a top plan view in cross-section of the toggle switch actuator assembly of FIG. 11 in a displaced position.

Another embodiment of the invention incorporates a toggle actuator assembly 300 as depicted in FIGS. 11 and 12. This embodiment again employs a master cylinder 322, a first slave cylinder 324, a second slave cylinder 326, and a fluid transfer cylinder 328 physically arranged and fluidly coupled with each other in a similar fashion to the hydraulic system of FIG. 1. The first slave cylinder 324 and the second slave cylinder 326 house a first slave piston 334 and a second slave piston 336, respectively, which in turn are attached to a first steering cable 338 and a second steering cable 340, respectively. The first and second steering cables 338, 340 are guided distally through the handle case 306 of the toggle actuator assembly 300 by proximal lateral guiding pins 346, a center guiding pin 348, and distal lateral guiding pins 350, similar to the arrangement of FIG. 1.

In this embodiment, the master shaft 330 acts in conjunction with the master piston 332 as a toggle. The master cylinder 322 of this embodiment is affixed to the handle case 306 by the cylinder fastener 342 and does not move. The lateral ends of the master shaft 330 are provided with a first toggle button 318a and a second toggle button 318b, respectively. In order to deflect the ablation tip on the end of an attached catheter, either the first or second toggle button 318a, 318b may be depressed laterally inward into the handle case 306, thereby displacing the master piston 332 within the master cylinder 322. For example, as shown in FIG. 12, the second toggle button 318b is pressed laterally inward into the handle case 306 forcing the master piston 332 rightward. This forces fluid within the master cylinder 322 into the first slave cylinder 324, which moves the first slave piston 334 distally within the first slave cylinder 324. Fluid on the distal side of the first slave piston 334 is forced into the fluid transfer cylinder 328, which further forces fluid into the second slave cylinder 326, forcing the second slave piston 336 in a distal direction.

As the first and second steering cables 338, 340 are attached to the first slave piston 334 and the second slave piston 336, respectively, the first steering cable 338 is moved distally, thereby reducing tension exerted by it on the ablation tip. The second steering cable 340 is moved proximally, thereby increasing the tension exerted by it on the ablation tip and thus deflecting the ablation tip. It should therefore be apparent that by alternatively depressing the first toggle button 318a, that an opposite hydraulic effect would be created and the ablation tip would be deflected in an opposite direction. As in the previous embodiments, the diameter of the master cylinder 322 is larger than the diameters of each of the first and second slave cylinders 324, 326, which thereby translates a small movement of the master shaft 330 into a larger linear displacement of the first and second steering cables 338, 340.

Figure 13:
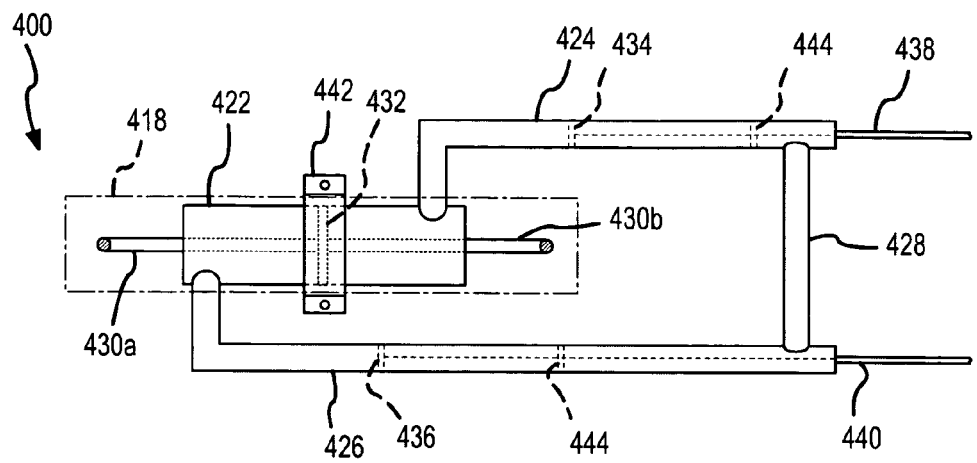
FIG. 13 is a top plan view of an additional embodiment of the present invention incorporating a sliding switch actuator assembly.
Figure 14:
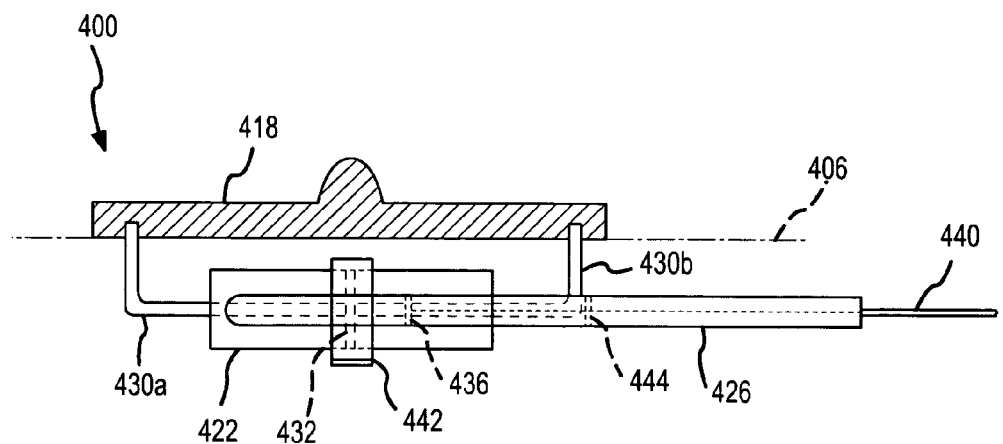
FIG. 14 is a side elevation view in partial cross-section of the sliding switch actuator assembly of FIG. 13.

Another embodiment of the invention, which incorporates a switch button actuator, is depicted in FIGS. 13 and 14. The hydraulic system of the switch button actuator assembly 400 includes a master cylinder 422 that is oriented parallel with the first and second steering cables 438, 440 rather than being oriented orthogonal to the first and second steering cables 438, 440 as in previous embodiments. The first slave cylinder 424 forms an L-shape with the foot of the L orthogonal to a side wall of the master cylinder 422 and positioned adjacent to the distal end of the master cylinder 422. The trunk of first slave cylinder 424 extends distally from the foot. The trunk section of the first slave cylinder 424 is much longer than the foot section to allow for greater travel distance of the first slave piston 434 and the first steering cable 438 housed inside. The second slave cylinder 426 is similarly L-shaped with the foot of the L orthogonal to the side wall of the master cylinder 422 and positioned adjacent to proximal end of the master cylinder 422. The trunk section of the second slave cylinder 426 is longer than the foot section to allow for greater travel distance of the second slave piston 436 and the second steering cable 440 housed within the second slave cylinder 426. A fluid transfer cylinder 428 connects the distal ends of the first and second slave cylinders 424, 426.

In this embodiment, the master shaft can be viewed as bifurcated with a proximal master shaft section 430a extending through the master cylinder 422 on the proximal side of the master piston 432, and a distal master shaft section 430b extending through the master cylinder 422 on the distal side of the master piston 432. Upon emerging from the master cylinder 422, each of the proximal and distal master shaft sections 430a, 430b bend upward to engage proximal and distal ends of a sliding switch actuator 418 positioned outside the handle actuator casing 406. The master cylinder 422 is fixedly attached to a surface of the switch button actuator assembly 400 by cylinder fastener 442. In this embodiment of the invention, the clinician can merely slide the switch actuator 418 proximally and distally to effect movement of the master piston 432 via the proximal and distal master shaft sections 430a, 430b. The movement of the master piston 432 within the master cylinder 422 translates a small linear movement of the switch actuator 418 into large travel distances of the first slave piston 434 and the second slave piston 436 in the first slave cylinder 424 and the second slave cylinder 426, respectively.

As shown in FIGS. 13 and 14, this embodiment of the invention employs piston stops 444 in each of the first and second slave cylinders 424, 426. These piston stops 444 may be hollow rings attached to the interior walls of the first and second slave cylinders 424, 426 to impede distal travel of the first and second slave pistons 434, 436 beyond the point of the pistons stops 444. The piston stops 444 may thus act as a safety feature to prevent excessive deflection of the ablation tip of a catheter or to insure that the first and second steering cables 438, 440 are not placed under excessive tensile force beyond their operating parameters.

Figure 15:
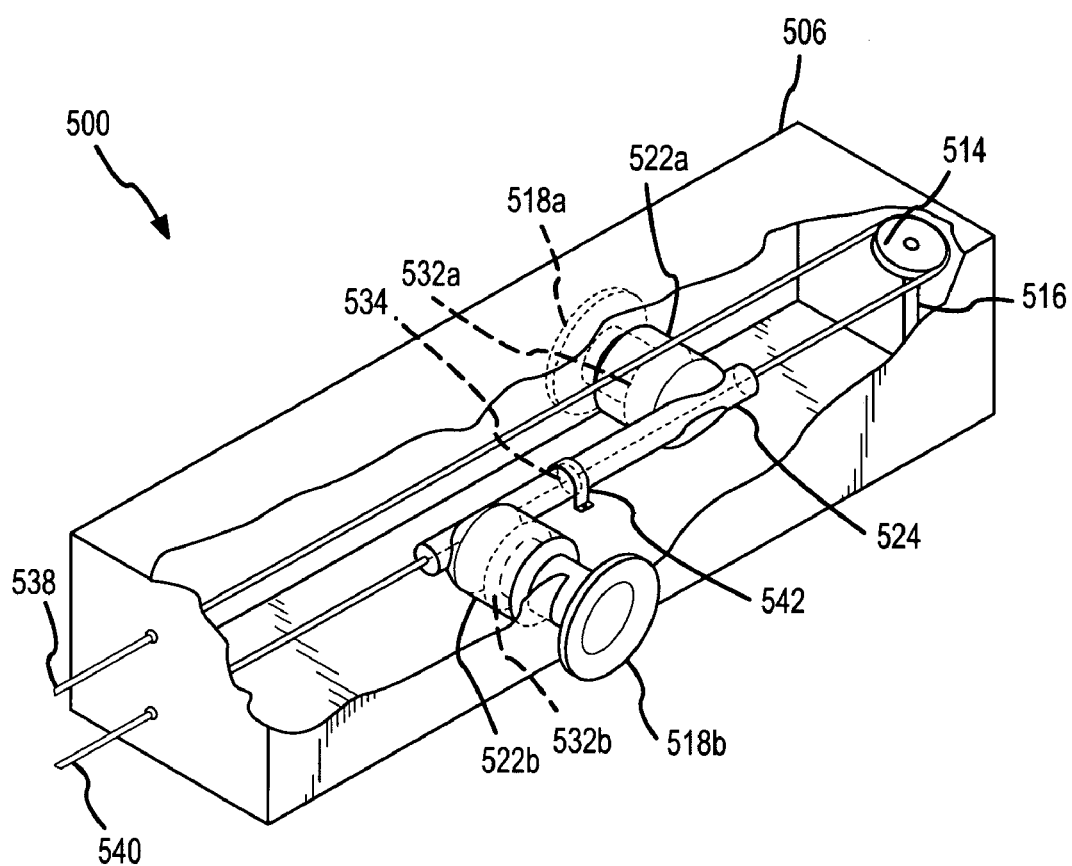
FIG. 15 is an isometric view in partial cut-away of a further embodiment of the present invention incorporating a push button actuator assembly.

A further embodiment of the invention is depicted in FIG. 15. This embodiment incorporates a push button actuator assembly 500 that includes a first master cylinder 522a, a second master cylinder 522b, and a single slave cylinder 524. The first and second master cylinders 522a, 522b are oriented parallel to each other but spaced apart from each other and are positioned on opposite ends of the slave cylinder 524. As shown in FIG. 15, the first master cylinder 522a is physically and fluidly coupled with the proximal end of the slave cylinder 524. Similarly, the second master cylinder 522b is physically and fluidly coupled with the distal end of the slave cylinder 524. A first push button actuator 518a is connected by a shaft to first master piston 532a, which resides within the first master cylinder 522a. The first push button actuator 518a extends laterally outside the handle case 506 for ease of actuation by a clinician. Similarly, a second push button actuator 518b is connected by a shaft to a second master piston 534b, which resides within the second master cylinder 522b. The second push button actuator 518b extends laterally outside of the handle case 506 to provide ease of access by a clinician.

As shown in FIG. 15, the slave cylinder 524 is affixed to the handle case 506 by cylinder fastener 542. A slave piston 534 is housed within the slave cylinder 524 and is attached on its proximal side to a first steering cable 538 and attached on its distal side to a second steering cable 540. The second steering cable 540 exits the distal end of the slave cylinder 524. The first steering cable 538 extends from the proximal end of the slave cylinder 524 to wrap around a proximal pulley 514 mounted on a proximal axel 516 within the handle case 506. Once the first steering cable 540 wraps around the proximal pulley 514, it extends out of the handle casing 506 in a distal direction.

In this embodiment, when the first push button actuator 518a is depressed, the first master piston 532a forces fluid within the first master cylinder 522a into the proximal end of the slave cylinder 524. This fluid movement forces the slave piston 534 to move distally thus increasing the tension on the first steering cable 538, which is translated around the proximal pulley 514 to bend the ablation tip of the attached catheter. As the slave piston 534 is pushed distally, fluid in the distal end of the slave cylinder 524 is forced into the second master cylinder 522b. This forces the second master piston 532b laterally outward within the second master cylinder 522b to accommodate the additional fluid.

Alternately, when the second push button actuator 518b is depressed by a clinician, a second master piston 532b forces fluid from the second master cylinder 522b into the distal end of the slave cylinder 524. This excess fluid in the distal end of the slave cylinder 524 forces the slave piston 534 to move proximally within the slave cylinder 524. As the second steering cable 540 is attached to the distal side of the slave piston 534, the second steering cable 540 is pulled proximally within the slave cylinder 524, increasing the tensile force placed on the second steering cable 538, and bending or deflecting the ablation tip of the attached catheter.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. An actuator assembly for a steerable catheter comprising a hydraulic system having
    a master cylinder having a first end and a second end;
    a first slave cylinder fluidly coupled with the first end of the master cylinder;
    a second slave fluidly coupled with the second end of the master cylinder;
    a first steering cable operably connected at a first end with the first slave cylinder and operably connected at a second end with a deflectable distal tip of a catheter;
    a second steering cable operably connected at a first end with the second slave cylinder and operably connected at a second end with the deflectable distal tip of the catheter; and
    a mechanical actuator, operably connected with the master cylinder, that imparts a mechanical force to the master cylinder.

2. The actuator assembly of claim 1 further comprising at least one translation member connected with both the mechanical actuator and the master cylinder to translate the mechanical force imparted by the mechanical actuator to the master cylinder.

3. The actuator assembly of claim 1, wherein the diameter of the master cylinder is greater than the diameter of at least one of the first slave cylinder and the second slave cylinder and the length of the master cylinder is less than the length of at least one of the first slave cylinder and the second slave cylinder.

4. The actuator assembly of claim 1 further comprising a master piston residing within the master cylinder;
    wherein the first slave cylinder is fluidly coupled with a first end of the master cylinder on a first side of the master piston, and
    the second slave cylinder is fluidly coupled with a second end of the master cylinder on a second side of the master piston.

5. The actuator assembly of claim 4 further comprising a fluid transfer cylinder fluidly coupled with both the first slave cylinder and the second slave cylinder.

6. The actuator assembly of claim 4, wherein
    the first slave cylinder and the second slave cylinder are each oriented generally parallel to an axis extending from a proximal end to a distal end of the actuator assembly; and
    the master cylinder is oriented transverse to each of the first slave cylinder and the second slave cylinder.

7. The actuator assembly of claim 6, wherein the master cylinder is positioned proximal to the first slave cylinder and the second slave cylinder.

8. The actuator assembly of claim 7, wherein the master cylinder is positioned distal to the first slave cylinder and the second slave cylinder.

9. The actuator assembly of claim 1 further comprising a handle; and wherein
    each of the master cylinder, the first slave cylinder, the second slave cylinder, and the mechanical actuator is pivotally mounted with respect to the handle.

10. The actuator assembly of claim 9, wherein the mechanical actuator comprises a substantially continuous wall and each of the master cylinder, the first slave cylinder, the second slave cylinder is positioned within an area bounded by the substantially continuous wall of the mechanical actuator.

11. The actuator assembly of claim 10, wherein the substantially continuous wall of the mechanical actuator forms a teardrop-shape and the mechanical actuator is mounted to the handle at a pointed apex of the teardrop-shape.

12. The actuator assembly of claim 11, wherein
    the mechanical actuator is mounted to the handle with the pointed apex of the teardrop-shape oriented distally;
    a channel is formed within the substantially continuous wall at the pointed apex of the teardrop-shape; and
    the first steering cable and the second steering cable each extend distally from the first slave cylinder and the second slave cylinder, respectively, through the channel, and into a lumen of the catheter.

13. The actuator assembly of claim 2, wherein the mechanical actuator further comprises at least one foot pedal.

14. The actuator assembly of claim 13, wherein
    the at least one translation member comprises a master shaft cable;
    the actuator assembly further comprises at least one pulley; and
    the master shaft cable is trained over the pulley to translate vertical movement imparted to the master shaft cable by the at least one foot pedal into horizontal movement.

15. The actuator assembly of claim 2 further comprising a master piston residing within the master cylinder; and wherein
    the translation member comprises
        a first master shaft connected with a first side of the master piston; and
        a second master shaft connected with a second side of the master piston; and the mechanical actuator comprises a toggle switch composed of
  a first toggle button attached to the first master shaft; and
  a second toggle button attached to the second master shaft.
16. The actuator assembly of claim 2 further comprising
a master piston residing within the master cylinder; and wherein
the translation member comprises
  a first master shaft connected with a first side of the master piston; and
  a second master shaft connected with a second side of the master piston; and
the mechanical actuator comprises a slide switch attached at a first end to the first master shaft and attached at a second end to the second master shaft.
17. The actuator assembly of claim 1, wherein the master cylinder further comprises
  a first master cylinder fluidly coupled with a proximal end of the at least one slave cylinder;
  a first master piston residing within the first master cylinder;
  a second master cylinder fluidly coupled with a distal end of the at least one slave cylinder; and
  a second master piston residing within the second master cylinder; and
the actuator mechanism further comprises
  a first push button actuator connected with the first master piston; and
  a second push button actuator connected with the second master piston.
18. The actuator assembly of claim 17, further comprising
a slave piston positioned within the at least one slave cylinder; and wherein
the at least one steering cable comprises a first steering cable and a second steering cable;
the first steering cable is operably connected at a proximal end with a proximal side of the first slave piston and operably connected at a distal end with the distal tip of the catheter, and
the second steering cable is operably connected at a proximal end with a distal side of the second slave piston and operably connected at a distal end with the distal tip of the catheter.
19. The actuator assembly of claim 18 further comprising
a pulley with which the first steering cable is operably connected to translate movement of the first steering cable from a first direction to a second direction.
20. An actuator assembly for a steerable catheter comprising
  a pneumatic system having a master cylinder;
  a plurality of fluidly independent slave cylinders fluidly coupled with both the master cylinder and a distal tip of a catheter; and
  a mechanical actuator, operably connected with the master cylinder, that imparts a mechanical force to the master cylinder, which increases fluid pressure in at least one of the plurality of slave cylinders and deflects the distal tip of the catheter.

* * * * *

UNITED STATES PATENT AND TRADEMARK OFFICE
CERTIFICATE OF CORRECTION

PATENT NO. : 7,717,875 B2
APPLICATION NO. : 10/895510
DATED : May 18, 2010
INVENTOR(S) : John Christian Knudson et al.

It is certified that error appears in the above-identified patent and that said Letters Patent is hereby corrected as shown below:

Column 17, claim 1, line 45, after slave, kindly insert --cylinder--.

Column 18, claim 8, line 22, kindly delete "7" and insert --6--.

Signed and Sealed this
Twelfth Day of March, 2013

Teresa Stanek Rea
*Acting Director of the United States Patent and Trademark Office*